(12) United States Patent
Jensen et al.

(10) Patent No.: US 10,786,805 B2
(45) Date of Patent: Sep. 29, 2020

(54) CADMIUM SULFIDE QUANTUM DOTS

(71) Applicant: Northwestern University, Evanston, IL (US)

(72) Inventors: Stephen C. Jensen, Chicago, IL (US); Emily A. Weiss, Chicago, IL (US)

(73) Assignee: Northwestern University, Evanston, IL (US)

( * ) Notice: Subject to any disclaimer, the term of this patent is extended or adjusted under 35 U.S.C. 154(b) by 496 days.

(21) Appl. No.: 15/074,169

(22) Filed: Mar. 18, 2016

(65) Prior Publication Data

US 2016/0288106 A1 Oct. 6, 2016

Related U.S. Application Data

(60) Provisional application No. 62/136,166, filed on Mar. 20, 2015.

(51) Int. Cl.
| | | |
|---|---|---|
| *B01J 27/04* | (2006.01) | |
| *B01J 35/00* | (2006.01) | |
| *B01J 19/12* | (2006.01) | |
| *C07C 211/46* | (2006.01) | |
| *B82Y 30/00* | (2011.01) | |

(52) U.S. Cl.
CPC ............ *B01J 27/04* (2013.01); *B01J 19/123* (2013.01); *B01J 19/127* (2013.01); *B01J 35/002* (2013.01); *B01J 35/004* (2013.01); *C07C 211/46* (2013.01); *B82Y 30/00* (2013.01); *Y10S 977/774* (2013.01)

(58) Field of Classification Search
None
See application file for complete search history.

(56) References Cited

U.S. PATENT DOCUMENTS

| | | | | |
|---|---|---|---|---|
| 3,338,806 A | * | 8/1967 | Harwood | .............. C25B 3/04 205/437 |
| 4,861,484 A | * | 8/1989 | Lichtin | .............. B01J 21/063 210/638 |
| 7,335,345 B2 | * | 2/2008 | Shih | .............. B82Y 5/00 252/301.4 F |
| 7,776,630 B1 | | 8/2010 | Kar et al. | |
| 8,426,728 B2 | | 4/2013 | Zhao et al. | |
| 8,858,832 B2 | | 10/2014 | Newkome et al. | |
| 2005/0163673 A1 | | 7/2005 | Johnson et al. | |
| 2005/0265935 A1 | | 12/2005 | Hollingsworth et al. | |
| 2011/0269243 A1 | * | 11/2011 | Strano | .............. B82Y 30/00 977/742 |

(Continued)

FOREIGN PATENT DOCUMENTS

| | | | |
|---|---|---|---|
| CN | 103084190 A | * | 5/2013 |
| WO | WO 2016/153989 | | 9/2016 |

OTHER PUBLICATIONS

Karwa et al, "Selective Catalytic Hydrogenation of Nitrobenzene to Phenylhydroxylamine," Ind. Eng. Chem. Res. 1987 vol. 26, pp. 1746-1750 (Year: 1987).*

(Continued)

*Primary Examiner* — Stephanie J Cohen
(74) *Attorney, Agent, or Firm* — Casimir Jones SC; David W. Staple

(57) ABSTRACT

Provided herein are compositions comprising cadmium sulfide quantum dot photocatalysts and methods and systems utilizing as much (e.g., for the reduction of a nitrobenzene to an aniline).

14 Claims, 10 Drawing Sheets

(56) References Cited

U.S. PATENT DOCUMENTS

| | | | |
|---|---|---|---|
| 2013/0206215 A1* | 8/2013 | Fuke | H01G 9/2031 136/254 |
| 2013/0207077 A1* | 8/2013 | Shih | H01L 33/26 257/13 |
| 2013/0240349 A1* | 9/2013 | Lian | B01J 19/127 204/157.52 |

OTHER PUBLICATIONS

Zhang et al, water soluble CdS quantum dots prepared from a refluxing single precursor in aqueous solution, j, phys chem B, 108, 18569-18574 (Year: 2004).*
Wu et al, a simple and highly efficient route for the preparation of p-phenylenediamine by reducing 4-nitroaniline over commercial CdS visible light-driven photocatalyst in water, green chem, 14, 1705-1709 (Year: 2012).*
Umar et al, Photocatalytic Degradation of Organic Pollutants in Water, Organic Pollutants—Monitoring, Risk and Treatment, pp. 195-208 (Year: 2013).*
Chang et al, photocatalytic reduction of o-chloronitrobenzene under visible light irradiation over CdS quantum dot sensitized TiO2, Phys Chem CHem Phyds, 2014, 16, pp. 16606-16614 (Year: 2014).*
Kumar et al, Synthesis of mercaptopropionic acid stabilized CDS quantum dots for bioimaging in breast cancer (Year: 2012).*
CN-103084190-A—English translation (Year: 2010).*
Acharya et al., The role of hole localization in sacrificial hydrogen production by semiconductor-metal heterostructured nanocrystals. Nano Lett. Jul. 13, 2011;11(7):2919-26.
Amirav et al., Luminescence studies of individual quantum dot photocatalysts. J Am Chem Soc. Sep. 4, 2013;135(35):13049-53.
Bernt et al., Photocatalytic carbon disulfide production via charge transfer quenching of quantum dots. J Am Chem Soc. Feb. 12, 2014;136(6):2192-5.
Berr et al., Delayed photoelectron transfer in Pt-decorated CdS nanorods under hydrogen generation conditions. Small. Jan. 23, 2012;8(2):291-7.
Boulesbaa et al., Ultrafast charge separation at CdS quantum dot/rhodamine B molecule interface. J Am Chem Soc. Dec. 12, 2007;129(49):15132-3.
Brown et al., Characterization of photochemical processes for H2 production by CdS nanorod-[FeFe] hydrogenase complexes. J Am Chem Soc. Mar. 28, 2012;134(12):5627-36.
Brown et al., Controlled assembly of hydrogenase—CdTe nanocrystal hybrids for solar hydrogen production. J Am Chem Soc. Jul. 21, 2010;132(28):9672-80.
Cass et al., Electronic and Vibrational Structure of Complexes of Tetracyanoquinodimethane with Cadmium Chalcogenide Quantum Dots. J. Phys. Chem. C, 2014, 118(31):18263-18270.
Cass et al., The chemical environments of oleate species within samples of oleate-coated PbS quantum dots. Anal Chem. Jul. 16, 2013;85(14):6974.
Chang et al., Ligand removal from CdS quantum dots forenhanced photocatalytic H2 generation in pH neutral water. J Mater Chem A. 2016;4:2856-62.
Chang et al., Photocatalytic reduction of o-chloronitrobenzene under visible light irradiation over CdS quantum dot sensitized TiO2. Phys Chem Chem Phys. 2014;16:16606-14.
Chaudhary et al., Visible light-driven CO2 reduction by enzyme coupled CdS nanocrystals. Chem Commun (Camb). Jan. 4, 2012;48(1):58-60.
Chauvire et al., Redox Photocatalysis with Water-Soluble Core-Shell CdSe—ZnS Quantum Dots. J. Phys. Chem. C 2015;119:17857-66.
Chen et al., Semiconductor-based photocatalytic hydrogen generation. Chem Rev. Nov. 10, 2010;110(11):6503-70.
Chi et al., Preparation and photoelectric performance of ITO/TiO2/CdS composite thin films. J. Photochem. Photobiol., A 2008;195:357-63.
Colvin et al., Valence-band photoemission from a quantum-dot system. Phys Rev Lett. May 27, 1991;66(21):2786-2789.
Cooney et al., Unified picture of electron and hole relaxation pathways in semiconductor quantum dots. Phys Rev B. 2007;75:245311.
Croston et al., Converstion of Aniline to Azobenzene at Fuctionalized Carbon Nanotubes: A Possible case of Nanodimensional Reaction. Int. J. Nanosci. 2002;1:285-293.
Das et al., Photogeneration of hydrogen from water using CdSe nanocrystals demonstrating the importance of surface exchange. Proc Natl Acad Sci U S A. Oct. 15, 2013;110(42):16716-23.
De Mello Donega et al., Size- and temperature-dependence of exciton lifetimes in CdSe quantum dots. Phys Rev B. 2006;74:085320.
Dukovic et al., Photodeposition of Pt on Colloidal CdS and CdSe/CdS Semiconductor Nanostructures. Adv Mater. Nov. 2008;20(22):4306-11.
Eggins et al., Formation of two-carbon acids from carbon dioxide by photoreduction on cadmium sulphide. J. Chem. Soc., Chem. Commun. 1988;16:1123-24.
Eskandari et al., Photocatalytic reduction of aromatic nitro compounds using CdS nanostructure under blue LED irradiation. 'Journal of Photochemistry & Photobiology, A: Chemistry' 274,7-12 (2014).
Forlano et al., The mechanism of oxidation of 3-mercaptopropionic acid. Can. J. Chem. 1997;75(1):9-13.
Frederick et al., Relaxation of exciton confinement in CdSe quantum dots by modification with a conjugated dithiocarbamate ligand. ACS Nano. Jun. 22, 2010;4(6):3195-200.
Gimbert-Surinach et al., Efficient and limiting reactions in aqueous light-induced hydrogen evolution systems using molecular catalysts and quantum dots. J Am Chem Soc. May 28, 2014;136(21):7655-61.
Gould et al., A Quantitative Comparison of the Photophysical Properties of Select Quantum Dots and Organic Fluorophores. Z. Phys. Chem. 2008;222:833-849.
Greene et al., Direct evidence of active-site reduction and photodriven catalysis in sensitized hydrogenase assemblies. J Am Chem Soc. Jul. 11, 2012;134(27):11108-11.
Han et al., Robust Photogeneration of H2 in Water Using Semiconductor Nanocrystals and a Nickel Catalyst. Science. Dec. 7, 2012;338(6112):1321-4.
Haram et al., Electrochemistry of CdS Nanoparticles: A Correlation between Optical and Electrochemical Band Gaps. J Am Chem Soc. Sep. 12, 2001;123(36):8860-1.
Harris et al., Semiconductors for Photoelectrolysis. Annu. Rev. Mater. Sci. 1978;8:99-134.
Hens et al., A Solution NMR Toolbox for Characterizing the Surface Chemistry of Colloidal Nanocrystals. Chem. Mater. 2013;25:1211-1221.
Hoffman et al., Photoinitiated polymerization of methyl methacrylate using Q-sized zinc oxide colloids. J. Phys. Chem. 1992;96:5540-6.
Hosokawa et al., Surface modification of CdS quantum dots with fluorinated thiophenol. J. Chem. Soc., Faraday Trans. 1996;92:4575-80.
Huang et al., Electroreduction of Chlorine Gas at Platinum Electrodes in Several Room Temperature Ionic Liquids: Evidence of Strong Adsorption on the Electrode Surface Revealed by Unusual Voltammetry in Which Currents Decrease with Increasing Voltage Scan Rates. J. Phys. Chem. C 2008;112(49):19734-83.
Huang et al., Photodriven charge separation dynamics in CdSe/ZnS core/shell quantum dot/cobaloxime hybrid for efficient hydrogen production. J Am Chem Soc. Oct. 10, 2012;134(40):16472-5.
Hurley et al., Photochemical n → π* Excitation of Nitrobenzene. J. Am. Chem. Soc. 1966;88:4330-32.
Inoue et al., Photocatalytic conversion of lactic acid to malic acid through pyruvic acid in the presence of malic enzyme and semiconductor photocatalysts. J. Chem. Soc., Faraday Trans. 1992;88:2215-19.
Iwasita, Electrocatalysis of methanol oxidation. Electrochim. Acta 2002;47:3663-74.
Jensen et al., Photocatalytic Conversion of Nitrobenzene to Aniline through Sequential Proton-Coupled One-Electron Transfers from a Cadmium Sulfide Quantum Dot. J Am Chem Soc. Feb. 10, 2016;138(5):1591-600.

(56) References Cited

OTHER PUBLICATIONS

Kisch, Semiconductor photocatalysis—mechanistic and synthetic aspects. Angew Chem Int Ed Engl. Jan. 14, 2013;52(3):812-47.

Klimov et al., Ultrafast dynamics of inter- and intraband transitions in semiconductor nanocrystals: Implications for quantum-dot lasers. Phys. Rev. B: Condens. Matter Mater. Phys. 1999; 60:R2177.

Knowles et al., A multi-timescale map of radiative and nonradiative decay pathways for excitons in CdSe quantum dots. ACS Nano. Mar. 22, 2011;5(3):2026-35.

Knowles et al., Exciton Dissociation within Quantum Dot—Organic Complexes: Mechanisms, Use as a Probe of Interfacial Structure, and Applications. J. Am. Chem Soc. C. 2013;117(20):10229-43.

Knowles et al., Spontaneous Multielectron Transfer from the Surfaces of PbS Quantum Dots to Tetracyanoquinodimethane. J. Am. Chem. Soc. 2013;135:7264-71.

Korgel et al., Quantum Confinement Effects Enable Photocatalyzed Nitrate Reduction at Neutral pH Using CdS Nanocrystals. J. Phys. Chem. B 1997;101:5010-17.

Kröhl et al., The electronic states of nitrobenzene: electron-energy-loss spectroscopy and CASPT2 calculations. Phys. Chem. Chem. Phys. 2, 947-953 (2000).

Kuehnel et al., Photocatalytic Formic Acid Conversion on CdS Nanocrystals with Controllable Selectivity for H2 or CO. Angew. Chem., Int. Ed. 2015;54:9627-31.

Kumar et al., Colloidal CdS-induced photocatalytic reaction of 2-methylindole—mechanistic analysis of oxidation of indoles. J. Phys. Org. Chem. 1998;11:277-82.

Lee et al., A Linker-Mediated Self-Assembly Method to Couple Isocharged Nanostructures: Layered Double Hydroxide—CdS Nanohybrids with High Activity for Visible-Light-Induced H2 Generation. Chem.—Eur. J. 2014;20:17004-10.

Li et al., An Exceptional Artificial Photocatalyst, Nih-CdSe/CdS Core/Shell Hybrid, Made in Situ from CdSe Quantum Dots and Nickel Salts for Efficient Hydrogen Evolution. Adv. Mater. 2013;25:6613-18.

Li et al., Electrochemical reduction of nitrobenzene at carbon nanotube electrode. Journal of Hazardous Materials. 2007;148:158-163.

Li et al., Mechanistic Insights into the Interface-Directed Transformation of Thiols into Disulfides and Molecular Hydrogen by Visible-Light Irradiation of Quantum Dots. Angew. Chem., Int. Ed. 2014;53:2085-89.

Liang et al., Branched Polyethylenimine Improves Hydrogen Photoproduction from a CdSe Quantum Dot/[FeFe]-Hydrogenase Mimic System in Neutral Aqueous Solutions. Chem.—Eur. J. 2015;21:3187-92.

Liu et al., Aqueous Photogeneration of H2 with CdSe Nanocrystals and Nickel Catalysts: Electron Transfer Dynamics. J. Phys. Chem. B 2015;119:7349-57.

Lund, Organic Electrochemistry; 4th ed.; Marcel Dekker: New York, 2001. Table of Contents Only.

Maldotti et al., Photochemical and photocatalytic reduction of nitrobenzene in the presence of cyclohexene. Journal of Photochemistry & Photobiology, A: Chemistry. 2000;133:129-133.

Malicki et al., Gating of hole transfer from photoexcited PbS quantum dots to aminoferrocene by the ligand shell of the dots. Chem. Commun. 2013;49:4400-02.

McArthur et al., Charge Carrier Resolved Relaxation of the First Excitonic State in CdSe Quantum Dots Probed with Near-Infrared Transient Absorption Spectroscopy. J. Phys. Chem. B 2010;114:14514-20.

Meng et al., CdSe quantum dots/molecular cobalt catalyst co-grafted open porous NiO film as a photocathode for visible light driven H2 evolution from neutral water. J. Mater. Chem. A 2015;3:18852-59.

Moreels et al., Size-Tunable, Bright, and Stable PbS Quantum Dots: A Surface Chemistry Study. ACS Nano 5, 2004-2012 (2011).

Morris-Cohen et al., Chemical, Structural, and Quantitative Analysis of the Ligand Shells of Colloidal Quantum Dots. Chem. Mater. 2013;25:1155-65.

Morris-Cohen et al., Simultaneous Determination of the Adsorption Constant and the Photoinduced Electron Transfer Rate for a Cds Quantum Dot—Viologen Complex. J. Am. Chem. Soc. 2011;133:10146-54.

Nedeljkovic et al., Enhanced photoredox chemistry in quantized semiconductor colloids. J. Phys. Chem. 1986;90:12-13.

Osterloh, Inorganic Materials as Catalysts for Photochemical Splitting of Water. Chem. Mater. 2008;20:35-54.

Pal et al., Photocatalytic syntheses of azoxybenzene by visible light irradiation of silica-coated cadmium sulfide nanocomposites. Chem. Commun. 2007;5:483-5.

Pal et al., Size and Structure-Dependent Photocatalytic Activity of Jingle-Bell-Shaped Silica-Coated Cadmium Sulfide Nanoparticles for Methanol Dehydrogenation. J. Phys. Chem. B 2004;108:18670-4.

Perera et al., Photocatalytic Activity of Core/Shell Semiconductor Nanocrystals Featuring Spatial Separation of Charges. J. Phys. Chem. C 2012;116:22786-93.

Peterson et al., Mechanisms for Adsorption of Methyl Viologen on CdS Quantum Dots. ACS Nano 2014;8:2826-37.

Pezzatini et al., Double-layer structure and mechanism of electrode reactions: Part II. Nitrobenzene reduction on mercury from aqueous solutions. J. Electroanal. Chem. 1979;2:205-19.

Phenylhydroxylamine, definiation, en.wikipedia.org/w/index.php?title=Phenylhydroxylamine&oldid=637397748, retrieved Jun. 27, 2016, 1 page.

Resch-Genger et al., Quantum dots versus organic dyes as fluorescent labels. Nat Methods. Sep. 2008;5(9):763-75.

Sachleben et al., Solution-State NMR Studies of the Surface Structure and Dynamics of Semiconductor Nanocrystals. J. Phys. Chem. B 1998;102:10117-10128.

Sarasa et al., Treatment of a wastewater resulting from dyes manufacturing with ozone and chemical coagulation. Water Research, 1998;32:2721-2727.

Scherer et al., Mass Transport Effects on the Kinetics of Nitrobenzene Reduction by Iron Metal. Environ. Sci. Technol. 2001;35:2804-2811.

Schrauben et al., Titanium and zinc oxide nanoparticles are proton-coupled electron transfer agents. Science. Jun. 8, 2012;336(6086):1298-301.

Shemesh et al., Synthesis and Photocatalytic Properties of a Family of CdS-PdX Hybrid Nanoparticles. Angew. Chem., Int. Ed. 2011;50:1185-9.

Shiragami et al., Semiconductor photocatalysis: visible light induced photoreduction of aromatic ketones and electron-deficient alkenes catalysed by quantised cadmium sulfide. J. Chem. Soc., Faraday Trans. 1992;88:1055-61.

Smith et al., Electrochemical reactions of organic compounds in liquid ammonia. II. Nitrobenzene and nitrosobenzene. J. Am. Chem. Soc. 1975;97:5203-10.

Soares et al., The in situ polymerization of aniline in nitrile rubber. Synthetic Metals. 2006;156:91-98.

Ten Cate et al., Generating Free Charges by Carrier Multiplication in Quantum Dots for Highly Efficient Photovoltaics. Acc. Chem. Res. 2015;48:174-81.

Terrill et al., Monolayers in three dimensions: NMR, SAXS, thermal, and electron hopping studies of alkanethiol stabilized gold clusters. J. Am. Chem. Soc. 1995;117:12537-12548.

Wang et al., A highly efficient photocatalytic system for hydrogen production by a robust hydrogenase mimic in an aqueous solution. Angew Chem Int Ed Engl. Mar. 28, 2011;50(14):3193-7.

Warrier et al., Photocatalytic reduction of aromatic azides to amines using CdS and CdSe nanoparticles. Photochem. Photobiol. Sci. 2004;3:859-63.

Wilker et al., Recent Progress in Photocatalysis Mediated by Colloidal II-VI Nanocrystals. Isr J Chem. Dec. 2012;52(11-12):1002-1015.

Worrell et al., Energy use and energy intensity of the U.S. chemical industry. LBNL-44314, Apr. 2000, https://pdfs.semanticscholar.org/099c/8d74f420b421d9188329c9f0f1e1f01acc55.pdf, retrieved Feb. 14, 2017,40 pages.

(56) References Cited

OTHER PUBLICATIONS

Wubbels et al., Hydrochloric-Acid Catalyzed Photoreduction of Nitrobenzene by 2-Propanol—Question of Protonation in Excited-State. J. Am. Chem. Soc. 1973;95(4):1281-1285.

Xiao et al., Layer-by-layer self-assembly of CdS quantum dots/graphene nanosheets hybrid films for photoelectrochemical and photocatalytic applications. J Am Chem Soc. Jan. 29, 2014;136(4):1559-69.

Yanagida et al., Semiconductor Photocatalysis: Size Control of Surface-Capped CdS Nanocrystallites and the Quantum Size Effect in Their Photocatalysis. Bull. Chem. Soc. Jpn. 1995;68:752.

Yang et al., Stable Quantum Dot Photoelectrolysis Cell for Unassisted Visible Light Solar Water Splitting. ACS Nano. Oct. 28, 2014;8(10):10403-13.

Yehezkeli et al., Electrostatically assembled CdS—Co3 O4 nanostructures for photo-assisted water oxidation and photocatalytic reduction of dye molecules. Small. Feb. 11, 2015;11(6):668-74.

Yu et al., Experimental Determination of the Extinction Coefficient of CdTe, CdSe, and CdS Nanocrystals. Chem. Mater. 2003;15:2854-60.

Yu et al., Nano-design of quantum dot-based photocatalysts for hydrogen generation using advanced surface molecular chemistry. Phys Chem Chem Phys. Jan. 14, 2015;17(2):1001-9.

Zhao et al., Quantum confinement controls photocatalysis: a free energy analysis for photocatalytic proton reduction at CdSe nanocrystals. ACS Nano. May 28, 2013;7(5):4316-25.

Zhu et al., Auger-assisted electron transfer from photoexcited semiconductor quantum dots. Nano Lett. Mar. 12, 2014;14(3):1263-9.

Zhu et al., Near unity quantum yield of light-driven redox mediator reduction and efficient H2 generation using colloidal nanorod heterostructures. J Am Chem Soc. Jul. 18, 2012;134(28):11701-8.

International Search Report and Written Opinion for PCT/US2016/023113, dated Jul. 28, 2016, 12 pages.

* cited by examiner

CADMIUM SULFIDE QUANTUM DOTS

CROSS REFERENCE TO RELATED APPLICATIONS

The present invention claims priority to U.S. Provisional Patent Application 62/136,166, filed Mar. 20, 2015, which is incorporated by reference in its entirety.

STATEMENT REGARDING FEDERALLY SPONSORED RESEARCH OR DEVELOPMENT

This invention was made with government support under DE-SC0001059 awarded by the Department of Energy; and W911NF-11-1-0075 awarded by the Army Research Office (ARO). The government has certain rights in the invention.

FIELD

Provided herein are compositions comprising cadmium sulfide quantum dot photocatalysts and methods and systems utilizing as much (e.g., for the reduction of a nitrobenzene to an aniline).

BACKGROUND

The advancement of next generation catalysts that operate at lower temperatures, in ambient conditions and which utilize renewable energy sources, such as sunlight, is of paramount importance to our society since the chemical industry is a large energy consumer in many countries (~7% in the US). Heterogeneous photocatalysts benefit from the ease of product separation because the catalyst is generally a solid while the reactants and products are liquid or gas, but these catalysts often have a lower activity compared to molecular catalysts due to their relatively low surface area to-volume ratio.

SUMMARY

Provided herein are compositions comprising cadmium sulfide quantum dot photocatalysts and methods and systems utilizing as much (e.g., for the reduction of a nitrobenzene to an aniline). In some embodiments, provided herein are compositions comprising cadmium sulfide quantum dots. In some embodiments, provided herein are systems comprising cadmium sulfide quantum dots and one or more of a nitrobenzene (e.g., nitrobenzene), a phenylhydroxylamine, and an aniline (e.g., aniline). In some embodiments, methods are provided for converting a nitrobenzene to an aniline comprising cadmium-sulfide-quantum-dot catalyzed photoreduction through a phenylhydroxylamine intermediate.

The compositions, systems and methods described herein find use, for example, in waste water remediation (e.g., converting a toxic nitrobenzene species into a much more benign aniline), green catalysis of industrially-applicable (e.g., used in many rubbers and dyes) aniline with energy from visible light, etc. In some embodiments, the catalysts described herein provide environmentally-friendly and less resource- and energy-intensive methods for producing aniline and phenylhydroxylamine from nitrobenzene. In some embodiments, systems operate at high nitrobenzene loading for chemical synthesis purposes or at low loading for environmental remediation purposes.

In some embodiments, provided herein are systems comprising: (a) a cadmium sulfide (CdS) quantum dot (QD); and (b) a nitrobenzene compound. In some embodiments, the nitrobenzene compound is selected from the group consisting of: nitrobenzene, 4-nitrobenzoic acid, methyl 4-nitrobenzoate, 1-chloro-4-nitrobenzene, 1-fluoro-4-nitrobenzene, 4-nitroaniline, 1-tertbutyl-4-nitrobenzene, 2,4,6-tri-tertbutyl-nitrobenzene, 1,3-dimethyl-2-nitrobenzene, 1,3-dimethyl-5-nitrobenzene, 2,4,6-trinitrotoluene, 2,4-dinitrotoluene, 2,6-dinitrotoluene, 2,3-dinitrotoluene, 2,5-dinitrotoluene, 3,4-dinitrotoluene, 3,5-dinitrotoluene, 1,3,5-trinitrobenzene, 2,4,6-trinitrophenol, and 2,4,6-trinitro-1,3-benzenediol. In some embodiments, the nitrobenzene compound is nitrobenzene.

In some embodiments, systems further comprise one or more solvents. In some embodiments, the solvent is water. In some embodiments, the solvent is methanol.

In some embodiments, systems further comprise one or more sacrificial reductants. In some embodiments, the sacrificial reductants comprise an alcohol, a thiol, a carboxylate, and/or ascorbic acid. In some embodiments, the sacrificial reductants is methanol and/or 3-mercaptopropionic acid.

In some embodiments, the system further comprises an aniline. In some embodiments, the aniline is a reduction produce of the nitrobenzene. In some embodiments, the aniline reduction product is selected from the group consisting of: aniline, 4-aminobenzoic acid, methyl 4-aminobenzoate, 1-chloro-4-aminobenzene, 1-fluoro-4-aminobenzene, 4-aminoaniline, 1-tertbutyl-4-aminobenzene, 2,4,6-tri-tertbutyl-aminobenzene, 1,3-dimethyl-2-aminobenzene, 1,3-dimethyl-5-aminobenzene, 2,4,6-triaminotoluene, 2,4-diaminotoluene, 2,6-diaminotoluene, 2,3-diaminotoluene, 2,5-diaminotoluene, 3,4-diaminotoluene, 3,5-diaminotoluene, 1,3,5-triaminobenzene, 2,4,6-triaminophenol, and 2,4,6-triamino-1,3-benzenediol. In some embodiments, the aniline compound is aniline.

In some embodiments, the system has a pH below 6.0 (e.g., between 2 and 5).

In some embodiments, the cadmium sulfide quantum dot is in solution. In some embodiments, the system further comprises a surface, wherein the cadmium sulfide quantum dot is adhered to the surface. In some embodiments, the surface is the interior of a vessel.

In some embodiments, provided herein are methods of reducing a nitrobenzene to an aniline comprising illuminating a system described herein with light at a wavelength between 350 nm and 450 nm (e.g., between 395 nm and 415 nm, between 400 nm and 410 nm, 405 nm, etc.).

In some embodiments, provided herein is a catalytic composition comprising: (a) CdS quantum dots; (b) solvent; and (c) a sacrificial reductant. In some embodiments, provided herein is a catalytic composition comprising: (a) CdS quantum dots; (b) water; (c) methanol; and (d) 3-mercaptopropionic acid.

In some embodiments, provided herein are methods of reducing a nitrobenzene to an aniline comprising exposing the nitrobenzene to a catalytic composition described herein and illuminating with light at a wavelength between 350 nm and 450 nm at an acidic pH. In some embodiments, the light is at a wavelength between 350 nm and 450 nm (e.g., between 395 nm and 415 nm, between 400 nm and 410 nm, 405 nm, etc.).

In some embodiments, in methods described herein aniline is produced from the nitrobenzene through a phenylhydroxylamine intermediate.

In some embodiments, provided herein are methods for converting a nitrobenzene to an aniline comprising cadmium-sulfide-quantum-dot catalyzed photoreduction through a phenylhydroxylamine intermediate.

DEFINITIONS

Figure 1:
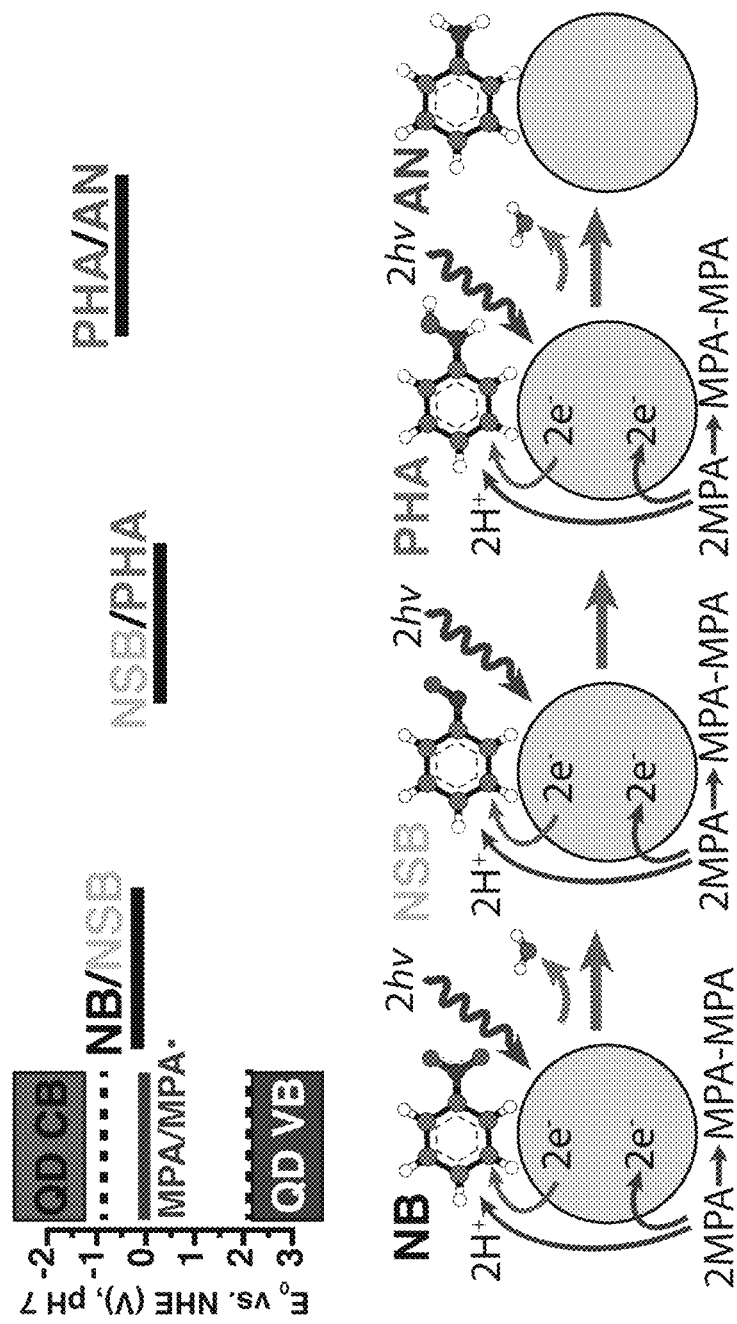
FIG. 1. Relevant proton-coupled electrochemical potentials (listed for a 1:1 water:methanol mix) (top) and mechanism (bottom) for the 6-electron, 6-proton reduction of nitrobenzene (NB) to aniline (AN) by photogenerated electron-hole pairs in a CdS QD through nitrosobenzene (NSB) and phenylhydroxylamine (PHA) intermediates. 3-mercaptopropionic acid (3-MPA) serves as the sacrificial reductant to regenerate the CdS QD catalyst, and as the proton donor for each reduction step. Water is a byproduct of steps 1 and 3. In the top diagram, the dotted lines correspond to the measured electrochemical band edges of N,N'-dimethylformamide-functionalized CdS QDs with a diameter of 3.9 nm, and boxes represent the valence and conduction bands for CdS QDs (diameter=4.5 nm). The valence band-edge is measured through photoemission spectroscopy and the conduction band edge equals the valence band edge plus the optical bandgap of the QDs.

As used herein, the term "nanoparticle" refers to a particle having a diameter between 1 and 100 nanometers. A nanoparticle may or may not exhibit one or more size-related properties that differ significantly from those observed in larger particles or bulk materials.

As used herein, the term "quantum dot" refers to a nanoparticle of one or more semiconductor materials in which electron (and/or exciton) propagation is confined in three spatial dimensions. Non-limiting examples of quantum dot materials include CdSe, CdS, ZnSe, ZnS, PbS, PbSe, CuS and combinations thereof.

As used herein, the term "photocatalyst" refers to any entity in which irradiation of such entity with electromagnetic radiation (e.g., visible or ultraviolet wavelength) results in the generation of conduction band electrons ($e_{cb}^-$) and valence band holes ($h_{vb}^-$) that can then undergo oxidation reactions at the catalyst surface with species such as water or other inorganic and organic compounds.

As used herein, the term "nitrobenzene" ("NB") refers to a compound having the structure:

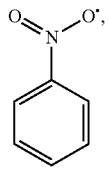

i.e., a benzene ring with an $NO_2^-$ substituent at the 1 position, without additional non-hydrogen substituents on the benzene ring.

As used herein, the terms "a nitrobenzene" "nitrobenzenes" refer to a compound having a base structure of nitrobenzene:

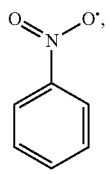

i.e., a benzene ring with an $NO_2^-$ substituent at the 1 position, and optionally also comprising one or more substituents (e.g., methyl group, chloro group, fluoro group, tert butyl group, amino group, additional nitro group(s), OH group, MeOH group, cyano etc.) at one or more of the 2, 3, 4, 5, and/or 6 positions. Exemplary nitrobenzenes include, for example, nitrobenzene, 4-nitrobenzoic acid, methyl 4-nitrobenzoate, 1-chloro-4-nitrobenzene, 1-fluoro-4-nitrobenzene, 4-nitroaniline, 1-tertbutyl-4-nitrobenzene, 2,4,6-tritertbutyl-nitrobenzene, 1,3-dimethyl-2-nitrobenzene, 1,3-dimethyl-5-nitrobenzene, 2,4,6-trinitrotoluene, 2,4-dinitrotoluene, 2,6-dinitrotoluene, 2,3-dinitrotoluene, 2,5-dinitrotoluene, 3,4-dinitrotoluene, 3,5-dinitrotoluene, 1,3,5-trinitrobenzene, 2,4,6-trinitrophenol, 2,4,6-trinitro-1,3-benzenediol, etc.

As used herein, the term "aniline" ("AN") refers to a compound having the structure:

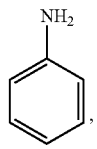

i.e., a benzene ring with an $NH_2$ substituent at the 1 position, and without additional non-hydrogen substituents on the benzene ring.

As used herein, the terms "an aniline" or "anilines" refers to a compound having a base structure of aniline:

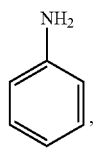

i.e., a benzene ring with an $NH_2$ substituent at the 1 position, and optionally also comprising one or more substituents (e.g., methyl group, chloro group, fluoro group, tert butyl group, amino group, additional nitro group(s), OH group, MeOH group, cyano etc.) at one or more of the 2, 3, 4, 5, and/or 6 positions. Exemplary anilines include, for example, aniline, 4-aminobenzoic acid, methyl 4-aminobenzoate, 1-chloro-4-aminobenzene, 1-fluoro-4-aminobenzene, 4-aminoaniline, 1-tertbutyl-4-aminobenzene, 2,4,6-tri-tert-butyl-aminobenzene, 1,3-dimethyl-2-aminobenzene, 1,3-dimethyl-5-aminobenzene, 2,4,6-triaminotoluene, 2,4-diaminotoluene, 2,6-diaminotoluene, 2,3-diaminotoluene, 2,5-diaminotoluene, 3,4-diaminotoluene, 3,5-diaminotoluene, 1,3,5-triaminobenzene, 2,4,6-triaminophenol, 2,4,6-triamino-1,3-benzenediol, etc.

DETAILED DESCRIPTION

Provided herein are compositions comprising cadmium sulfide quantum dot photocatalysts and methods and systems utilizing such photocatalysts to carry out chemical reactions (e.g., for the reduction of a nitrobenzene to an aniline).

Quantum dots (QDs) have the potential to combine the benefits of heterogeneous catalysts such as a high molar extinction coefficient and high photo-stability present in bulk semiconductors with the advantages of homogeneous catalysts such as high activity and selectivity per unit volume. Previous reports have combined quantum confined systems with a homogeneous catalyst, such as colloidal nickel (ref. A2; incorporated by reference in its entirety), NiO (ref. A3; incorporated by reference in its entirety), or Fe—Fe hydrogenases (ref. A4; incorporated by reference in its entirety), and demonstrated that these coupled systems are active toward hydrogen gas evolution.

In some embodiments, provided herein are systems and materials in which quantum dots act as catalysts to drive or catalyze non-spontaneous chemical reactions in the presence of radiation (e.g., visible, ultraviolet, etc.). Following light absorption, the QDs transfer one or more charges (either electrons or electron-holes) from the QD to molecular reactants and intermediates to facilitate and otherwise unfavorable (or less favorable) chemical reactions. A photocatalytic device that comprises such a system is also provided.

Experiments conducted during development of embodiments of the present invention demonstrate that the QD surface itself is catalytically active toward nitrobenzene (NB) photo-reduction to aniline (AN) via a phenylhydroxylamine (PHA) intermediate in aqueous solution at pH 4.3. The activity of the QDs (electrons transferred·g catalyst$^{-1}$·J photons$^{-1}$) is between $1.5 \times 10^6$ and $4 \times 10^8$ times higher than previous reports utilizing CdS powder (refs. A5, A6; incorporated by reference in their entireties) which required stirring to remain in solution. Aniline is important industrially, for example, as a precursor for dyes (ref. A7; incorporated by reference in its entirety), pesticides, and as a rubber additive (ref. A8; incorporated by reference in its entirety) with one million tons produced annually.

Experiments described herein demonstrate that in addition to their activity, QDs are stable even after transferring up to 4.5 million electrons per QD to adsorbed nitrobenzene molecules. Aniline desorption from the QD is a rate limiting step when the turn over number per QD exceeds the available binding sites, and under mild acidic conditions aniline is protonated, thus increasing its solubility which increases the turnover number (nitrobenzene molecules reduced) from $3.0 \times 10^2$ molecules per QD to $8.25 \times 10^5$ molecules per QD over 54 hours.

Experiments conducted during development of embodiments herein demonstrate that CdS QDs are active toward NB photo-reduction and that a single QD is capable of reducing 825,000 NB molecules over 54 hours of illumination. This turnover number (TON) corresponds to the transfer of 4.5 million electrons from each QD to adsorbed NB and various photoproducts. The activity of the catalyst (per g·J photon) is a factor of $10^6$-$10^8$ higher than previous reports with CdS powder (refs. A5,6; incorporated by reference in their entireties). 3-MPA acts as both a hole scavenger and as a proton source for the proton coupled electron transfer steps of the nitrobenzene reduction. The action spectrum for photoreduction of NB overlays the absorbance spectrum of the QDs. This result indicates that the reduction of NB to AN though NSB and PHA intermediates occurs by direct donation of photo-generated electrons in the QD to the catalytic substrates, without the need of a tethered molecular catalyst to act as an electron shuttle.

Quantitative NMR analysis of this reaction shows that, upon mixing of QDs with NB, a small fraction (18%) of added NB binds to the surface of QDs, but that the photoproduct AN binds strongly to the QDs, and implicates adsorbed AN as a poison for the QD catalyst. The differences in solubility of aniline and its protonated form, anilinium, in a water/methanol mix are utilized to modulate the desorption of AN (e.g., the rate-limiting step of the reaction). Under neutral pH conditions AN stays bound to the QD after formation, and thereby limits the TON to $3.0 \times 10^2$ molecules per QD, but by tuning the pH to <4.6 with 3-MPA, the TON is increased by a factor of 2750. Incidentally, running the reaction under neutral pH conditions allows detection of the number of catalytic sites on the QD (equal to the number of adsorbed AN molecules per QD), which for these CdS QDs is 52. The QDs operate under visible illumination at room temperature, in contrast to the conventional industrial synthesis of AN, which requires refluxing NB at 250° C. in the presence of a tin catalyst.

In some embodiments, systems and methods are provided in which a QD catalyst facilitates or drives forward the conversion of reduction of a nitrobenzene (e.g., nitrobenzene, substituted nitrobenzene, etc.) to an aniline (e.g., aniline, substituted aniline, etc.). In some embodiments, nitrobenzene (

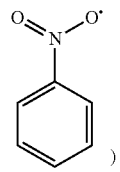

)

is reduced to aniline (

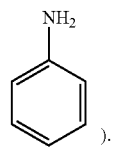

).

In other embodiments, a nitrobenzene derivative is converted into a aniline derivative. Experiments conducted during development of embodiments herein have demonstrated the reduction of multiple nitrobenzenes (e.g., 4-nitrobenzoic acid to 4-aminobenzoic acid, methyl 4-nitrobenzoate to methyl 4-aminobenzoate, 1-chloro-4-nitrobenzene to 1-chloro-4-aminobenzene, 1-fluoro-4-nitrobenzene to 1-fluoro-4-aminobenzene, 4-nitroaniline to 4-aminoaniline, 1-tertbutyl-4-nitrobenzene to 1-tertbutyl-4-aminobenzene) and similar compounds (e.g., 4-nitronapthalene to 4-aminonapthalene). In some embodiments, provided herein is the CdS-photocatalyzed reduction of other nitrobenzenes (e.g., 2,4,6-tri-tertbutyl-nitrobenzene to 2,4,6-tri-tertbutyl-aminobenzene, 1,3-dimethyl-2-nitrobenzene to 1,3-dimethyl-2-aminobenzene, 1,3-dimethyl-5-nitrobenzene to 1,3-dimethyl-5-aminobenzene, 2,4,6-trinitrotoluene to 2,4,6-triaminotoluene, 2,4-dinitrotoluene to 2,4-diaminotoluene, 2,6-dinitrotoluene to 2,6-diaminotoluene, 2,3-dinitrotoluene to 2,3-diaminotoluene, 2,5-dinitrotoluene to 2,5-diaminotoluene, 3,4-dinitrotoluene to 3,4-diaminotoluene, 3,5-dinitrotoluene to 3,5-diaminotoluene, 1,3,5-trinitrobenzene to 1,3,5-triaminobenzene, 2,4,6-trinitrophenol to 2,4,6-triaminophenol, 2,4,6-trinitro-1,3-benzenediol to 2,4,6-triamino-1,3-benzenediol, etc.). In some embodiments, provided herein is the CdS-photocatalyzed reduction of compounds similar to nitrobenzenes (e.g., nitroglycerine, 2,4,6-trinitrophenol, 2,4,6-trinitro-1,3-benzenediol, 1,3,5-Trinitroperhydro-1,3,5-triazine (RDX), Octahydro-1,3,5,7-tetranitro-1,3,5,7-tetrazocine (HMX), Hexanitrohexaazaisowurtzitane (CL-20), Octanitrocubane (ONC), Heptanitrocubane, etc.).

In some embodiments, a nitrobenzene reactant is present in a concentration between 100 µM and 100 mM (e.g., 100 µM, 200 µM, 500 µM, 1 mM, 2 mM, 4 mM, 8 mM, 10 mM, 20 mM, 50 mM 100 mM, and ranges there between).

In some embodiments, the systems and methods described herein find use in the conversion of the high-toxic nitrobenzene into the commercially-valuable aniline. Embodiments find use in the commercial and/or industrial production of anilines (e.g., anilines), at a variety of production scales (e.g., <1 L, 1 L, 2 L, 5 L, 10 L, 20 L, 50 L 100 L, 200 L, 500 L, 1000 L, 2000 L, 5000 L, 10,000 L, or more, or ranges there between). Embodiments also find use in remediating nitrobenzene pollutants or side products from chemical or industrial processes.

In certain embodiments, cadmium sulfide (CdS) quantum dots are utilized as the photocatalyst in the embodiments herein. However, the scope herein is not limited to such embodiments. In other embodiments, quantum dots of CdSe, ZnSe, ZnS, PbS, PbSe, CuS and combinations thereof are utilized as photocatalysts for the conversion of nitrobenzenes (or variants thereof) to anilines (or variants thereof). However, embodiments will be described herein with reference to CdS quantum dots. In some embodiments, CdS photocatalysts comprise quantum dots of 1-10 nm in size (e.g., 1 nm, 2 nm, 3 nm, 4 nm, 5 nm, 6 nm, 7 nm, 8 nm, 9 nm, 10 nm, and any ranges therein (e.g., 2 to 7 nanometers)) with their optical properties spanning the UV to blue spectral window (e.g., 350 to 450 nm (e.g., 350 nm, 360 nm, 370 nm, 380 nm, 390 nm, 400 nm, 405 nm, 410 nm, 420 nm, 430 nm, 440 nm, 450 nm, or ranges there between), 390 nm to 420 nm, 400 nm to 410 nm, etc.), depending on QD size (e.g., smaller size QDs require higher energy light).

In some embodiments, QDs are provided as modified QDs, coated QDs (e.g., zinc coated), surface-functionalized quantum dots, etc. For example, QDs may be coated to reduce potential toxicity from heavy metals. Methods and modifications are known in the field, as described in, for example, U.S. Pat. Nos. 8,858,832, 7,776,630, 2005/0265935, 8,426,728; incorporated by reference in their entireties.

In some embodiments, a QDs (e.g., CdS QDs) are present in a concentration between 1 nm and 1 µM (e.g., 1 nm, 2 nm, 5 nm, 10 nm, 20 nm, 50 nm, 100 nm, 200 nm, 500 nm, 1 µM, and ranges there between).

In some embodiments, within the systems described herein each CdS QD is capable of catalyzing the transfer of at least 10,000 electrons per hour (e.g., 10,000, $e^- h^{-1}$, 20,000 $e^- h^{-1}$, 30,000 $e^- h^{-1}$, 40,000 $e^- h^{-1}$, 50,000 $e^- h^{-1}$, 60,000 $e^- h^{-1}$, 70,000 $e^- h^{-1}$, 80,000 $e^- h^{-1}$, 90,000 $e^- h^{-1}$, 100,000 $e^- h^{-1}$, 150,000 $e^- h^{-1}$, 200,000 $e^- h^{-1}$, 300,000 $e^- h^{-1}$, 400,000 $e^- h^{-1}$, 500,000 $e^- h^{-1}$, and ranges there between).

In some embodiments, CdS QDs catalyze the conversion of nitrobenzenes (or variants thereof) to anilines (or variants thereof). In some embodiments, one or more solvents are provided in which both the QDs and reactant nitrobenzene (or substituted nitrobenzene) are soluble. In some embodiments, the solvent is water. In some embodiments, water is provided with a co-solvent. In some embodiments, at least 10% of the solvent provided is water (e.g., 10%, 20%, 30%, 40%, 50%, 60%, 70%, 80%, 90%, 100%, or ranges there between). In some embodiments, a solvent or co-solvent is methanol, ethanol or another alcohol (e.g., present at 10-100% (e.g., 10%, 20%, 30%, 40%, 50%, 60%, 70%, 80%, 90%, 100%, or ranges there between), etc.). In some embodiments in which methanol or another alcohol is used as a solvent or co-solvent, methanol or another alcohol also serves as a sacrificial reductant or co-sacrificial reductant. In some embodiments, benzene or another organic solvent is provided as a solvent or co-solvent. Any organic solvent known in the art may find use in embodiments herein, provided that the CdS QDs and the nitrobenzene reactant are soluble in the final solvent composition.

In some embodiments, in addition to the solvent, QDs, and reactant (e.g., nitrobenzene) an additional sacrificial reductant is provided in the reaction solution (or mixture). The sacrificial reductant serves to (i) regenerate the CdS QD catalyst, and (ii) act as the proton donor for the reduction steps. In some embodiments, a sacrificial reductant is an alcohol (e.g., methanol, ethanol, isopropanol, etc.), thiol (e.g., 3-mercaptopropionic acid), a combination thereof (e.g., β-mercaptoethanol), a carboxylate (e.g., formate ion, acetate ion, lactate ion, oxalate ion, citrate ion, etc.), ascorbic acid, etc. In some embodiments, the sacrificial reductant is provided in a stoichiometric ratio with respect to the reactant (e.g., nitrobenzene), for example, 20:1, 15:1, 10:1, 8:1, 6:1, 5:1, 4:1, 3:1, 2:1, 1:1, 2:1, 3:1, 4:1, 5:1, 6:1, 7:1, 8:1, 9:1, 10:1, 15:1, 20:1, or ranges there between).

In some embodiments, the reaction is carried out under acidic conditions (e.g., <pH 7.0). In some embodiments, lower pH speeds the reaction (e.g., toward completion), and, along with the presence of an appropriate sacrificial reductant, facilitates desorption of the aniline from the QD (a rate-limiting step in the reaction). In some embodiments, the reaction is carried out at an acidic pH, such as: pH 2.0, pH 2.4, pH 2.8, pH 3.2, pH 3.6, pH 4.0, pH 4.4, pH 4.8, pH 5.2, pH 5.6, pH 6.0, pH 6.4, or any ranges there between (e.g., pH 2-4, pH 3.2-5.4, etc.).

In some embodiments, the photocatalytic reaction is driven by exposure to the appropriate wavelength of light. In some embodiments, the necessary wavelength is determined by the chemical composition and size of the quantum dots used. The most suitable wavelength and QD identity may vary for different applications, scales (e.g., industrial, research, etc.) and environments (e.g., in a chemical reactor, outdoors, etc.). As addressed above, photocatalysis may be driven by exposure to light between 350 and 450 nm (e.g., 350 nm, 360 nm, 370 nm, 380 nm, 390 nm, 400 nm, 405 nm, 410 nm, 420 nm, 430 nm, 440 nm, 450 nm, or ranges there between), 390 nm to 420 nm, 400 nm to 410 nm, etc.), depending on QD size and composition.

In some embodiments, the reaction is carried out in solution, with the QDs, reactant (e.g., nitrobenzene), solvents, sacrificial reductant, etc. all together in solution contained in a reaction volume (e.g., chemical reactor (e.g., research reactor, commercial reactor, industrial reactor, etc.), glassware, etc.). In some embodiments, the QDs are adhered to a surface (e.g., a reaction card, a plate, the interior surface of a volume (e.g., vial, chemical reactor, etc.), a chip, etc. and the reactant (e.g., nitrobenzene) and the other components are passed over the surface. In some embodiments, a catalytic solution (e.g., comprising QDs, solvent, and sacrificial reductant) is applied to the reactant (e.g., in a volume, in a contaminated area) to initiate conversion.

In some embodiments, the photocatalytic reaction is carried out in a chemical reactor. In some embodiments, the reactor is of the appropriate scale for the particular application (e.g., <1 L, 1 L, 2 L, 5 L, 10 L, 20 L, 50 L 100 L, 200 L, 500 L, 1000 L, 2000 L, 5000 L, 10,000 L, or more, or ranges there between). In some embodiments, a chemical reactor is a batch-style reactor, tank reactor, continuous stirred-tank reactor (CSTR), a plug flow reactor (e.g., with QDs adhered to the internal surface and liquid reagents passed through), a semi-batch reactor, etc. In some embodiments, a reactor comprises a window or translucent/transparent portion to allow illumination with the appropriate wavelength of light. In some embodiments, a reactor is transparent to the appropriate wavelength of light. In some embodiments, a reactor comprises an internal light source for illumination.

In some embodiments, all reagents are added to the reactor and the reaction proceeds to completion or an acceptable end point. In some embodiments, the product is removed as the reaction proceeds. In some embodiments, additional reactant is added as the reaction proceeds. In some embodiments, a reactor comprises one or more ports, valves, etc. for introduction and/or removal of reactants, products, etc.

EXPERIMENTAL

Example 1

Materials and Methods

Oleate Capped CdS QD Preparation.

In a 3-neck round-bottomed flask, 0.256 g CdO, 13.7 mL octadecene (ODE), and 6.3 mL oleic acid (OA) were heated to 250° C. under a flow of nitrogen. It was ensured that CdO was all converted to Cd Oleate by checking that the solution is clear, and 4 mL of the solution was removed and the rest was stored. The 4 mL Cd Oleate was combined with 6 mL ODE and the solution was heated under nitrogen to 260° C. To initiate the QD growth, 2 mL 0.10 M sulfur in ODE was injected and the temperature was reduced to 220° C. The oleate-capped QDs nucleated for 1.5 minutes and it was verified that they have a first absorption peak in the UV-Vis spectrometer at ~407 nm. The QDs were purified by splitting the QD mixture into 4×15 mL centrifuge tubes and adding 3:1 acetone:QDs. The tubes were centrifuged at 3500 rpm for 5 minutes. The supernatant was yellow and the pellet of QDs was bright yellow. The supernatant was discarded and the pellet redispersed in 1-2 mL hexanes, adding 3:1 methanol:QDs. The redispersed pellet was centrifuged at 3500 rpm for 5 minutes, the supernatant was discarded, and the pellet redispersed in chloroform. The QDs sat for at least 24 hours before any additional treatment.

3-MPA Ligand Exchange for Oleate Capped CdS.

A ligand exchange was conducted to remove oleate ligands and exchange with 3-MPA ligands. The QDs were exchanged as needed, since they are sensitive to oxygen and crash out of solution over time, but these volumes are for one batch of oleate capped QDs listed above. The QDs were concentrated to occupy 0.25 mL or less, and 0.5 mL 3-MPA, 6 mL methanol, and 7 mL Triton B was added. The solution was stirred for at least 2.5 hr and transferred to 4×15 mL centrifuge tubes. 5 mL ethyl ether and 5 mL ethyl acetate was added to each tube and centrifuged at 3500 rpm for 5 minutes. The supernatant was discarded, and the pellet redisperse in 4 mL methanol, then mixed with 5 mL ethyl ether and 5 mL ethyl acetate, centrifuged the tubes again at 3500 rpm for 5 minutes, removed the supernatant, and redispersed in methanol. The solution was purged with nitrogen or argon for 5 minutes and stored in a nitrogen box for 24 hours before experiments.

QD Action Spectra Calculation

The concentration of NB was calculated for each sample with 1H-NMR and the area of the phenyl ring protons was interrogated against a known standard. The sample was illuminated with a commercial Ti-sapphire laser (Spitfire, 1 kHz, 100 fs, Spectra Physics), which is guided into an optical parametric amplifier (TOPAS-C, Light Conversion) to provide a tunable source between 360-460 nm used for these experiments. The wavelength was confirmed with a spectrometer and the incident power with a power meter. The absorbance of the QDs is measured in a 1-cm cuvette from a UV-Vis spectrometer and the expected absorbance was determined for the smaller GC vial used for the illumination, which allowed calculation of the expected power absorbed by the QDs. The number of nitrobenzene molecules reduced per photon absorbed is then calculated:

NB Reduced/Photons Absorbed=$NB$ Reduced/(Photons$_{abs}$/QDs$_{total}$).

PHA and AN Product Quantification from GC-MS

The concentration of PHA and AN was calculated by first running a concentration curve for each molecule in the GC-MS. Both PHA and AN desorb exclusively as AN from the GC-column, however the integrated signal intensity for PHA at a particular concentration is ~10% of what would be expected for aniline at the same concentration. Since it is known from NMR that the concentration of aromatic molecules is conserved during the photo-reduction of nitrobenzene, and that the only products are phenylhydroxylamine and aniline, the smaller apparent product yield is instead due to the smaller cracking fraction of phenylhydroxylamine compared to aniline. The concentrations of aniline and phenylhydroxylamine can thus be determined by calculating the concentration of products from the amount of remaining nitrobenzene (equation 1a), setting the signal of apparent products equal to a sum of both phenylhydroxylamine and aniline calibration curves (equation 1b), and solving for the concentration of phenylhydroxylamine and aniline.

$$[\text{Products}]_t=[NB]_0-[NB]_t \quad \text{(Equation 1a)}$$

$$MS\ \text{ProductSignal}_t=f([NB]_t)-g([NB]_t) \quad \text{(Equation 1b)}$$

3-MPA is Reduced to 3, 3-Dithiodipropionic Acid as a Result of the Photo-Reduction.

Figure 5:
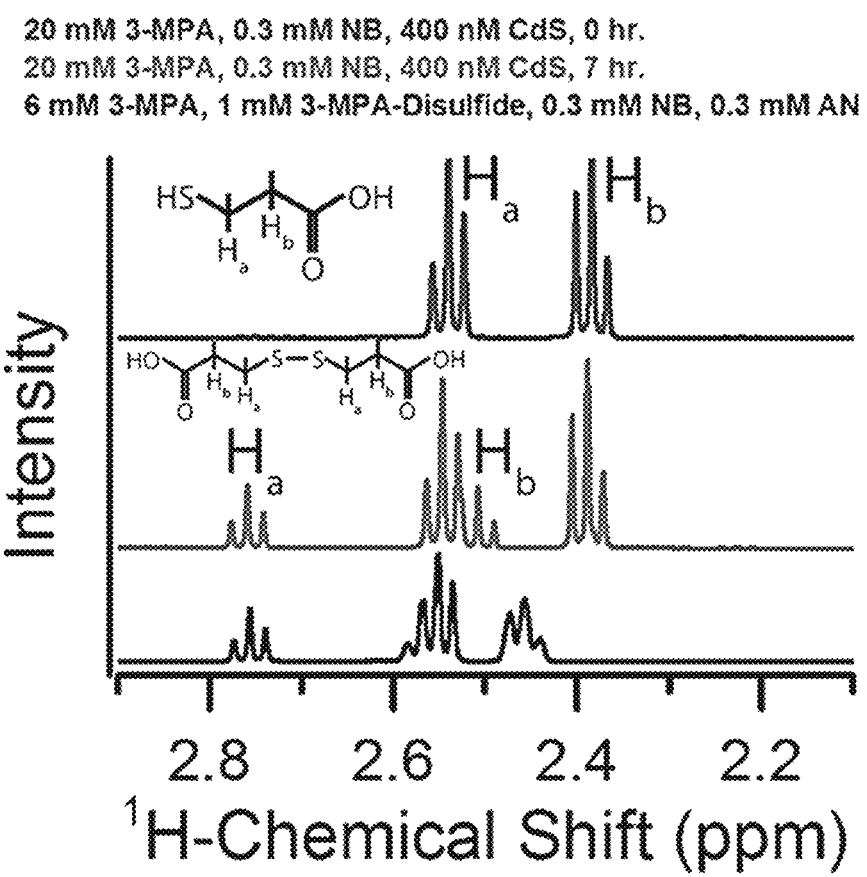
FIG. 5. $^1$H-NMR spectra of the H-C region of 3-MPA of a solution of 4 mM nitrobenzene, 20 mM 3-MPA, and 400 nM CdS QDs in 80:20 CD3OD:D2O prior to illumination (top) and after 7 hr of illumination (middle). Also shown is the spectrum of a control sample, 1 mM 3-MPA disulfide, 6 mM 3-MPA, 0.3 mM NB, and 0.3 mM AN dissolved in 80:20 CD3OD:D2O (bottom).

1H-NMR results reveal that prior to illumination a 80:20 CD3OD:D2O solution containing 4 mM nitrobenzene, 20 mM 3-MPA, and 400 nM CdS QDs show two triplet peaks near 2.5 ppm that are characteristic of 3-MPA (FIG. 5—bottom). Upon illumination, the peak intensity drops and a new set of triplet peaks form, which are shifted 0.2 ppm downfield (FIG. 5—middle). A comparison of these peaks to the MPA-MPA disulfide (FIG. 5—top) reveals that as nitrobenzene is being reduced, 3-MPA is being oxidized to the disulfide form to maintain charge neutrality in the overall system.

GC-MS Kinetic Modeling

The rate equation for 3 sequential, reversible reactions is as follows:

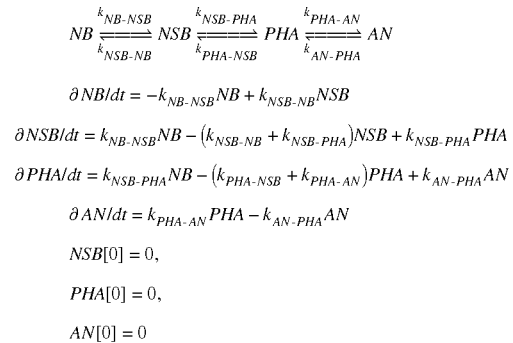

The rates kNB-NSB, kNSB-PHA, kPHA-AN designate the forward reactions while kNSB-NB, kPHA-NSB, kAN-PHA are the back reactions. The starting concentration for all products are set to 0, while (NB) is allowed to float. Mathematica 10 was utilized for symbolically deriving the differential equations. Mathematica was unable to compute the symbolic solution to the set of differential equations with all six rates, so the system was first solved for the forward reactions only to derive approximate solutions for the kinetic rates and the initial NB concentration.

$$[NB]_t = [NB]_0 e^{-tk_{NB-NSB}}$$

$$[NSB]_t = \frac{-[NB]_0 k_{NB-NSB} e^{-tk_{NB-NSB} - tk_{NSB-PHA}} \left(-e^{tk_{NB-NSB}} + e^{tk_{NSB-PHA}}\right)}{k_{NB-NSB} - k_{NSB-PHA}}$$

$$[PHA]_t = ([NB]_0 k_{NB-NSB} k_{NSB-PHA} e^{-tk_{NB-NSB} - tk_{NSB-PHA} - tk_{PHA-AN}}$$
$$(k_{NB-NSB} e^{tk_{NB-NSB} + tk_{NSB-PHA}} -$$
$$k_{12} e^{tk_{NB-NSB} + tk_{PHA-AN}} -$$
$$k_{23} e^{tk_{NB-NSB} + tk_{NSB-PHA}} +$$
$$k_{NSB-PHA} e^{tk_{NSB-PHA} + tk_{PHA-AN}} +$$
$$k_{PHA-AN} e^{tk_{NB-NSB} + tk_{PHA-AN}} -$$
$$k_{PHA-AN} e^{tk_{NSB-PHA} + tk_{PHA-AN}})) /$$
$$((k_{NB-NSB} - k_{NSB-PHA})(k_{NB-NSB} -$$
$$k_{NSB-PHA})(k_{NSB-PHA} - k_{PHA-AN}))$$

$$[AN]_t = ([NB]_0 e^{-tk_{NB-NSB} - tk_{NSB-PHA} - tk_{PHA-AN}}$$
$$(-k_{NB-NSB}^2 k_{NSB-PHA} e^{tk_{NB-NSB} + tk_{NSB-PHA}} +$$
$$k_{NB-NSB}^2 k_{NSB-PHA} e^{tk_{NB-NSB} + tk_{NSB-PHA} + tk_{PHA-AN}} -$$
$$k_{NB-NSB}^2 k_{NSB-PHA} e^{tk_{NB-NSB} + tk_{NSB-PHA}} -$$
$$k_{NB-NSB}^2 k_{NSB-PHA} e^{tk_{NB-NSB} + tk_{NSB-PHA} + tk_{PHA-AN}} +$$
$$k_{NB-NSB}^2 k_{PHA-AN} e^{tk_{NB-NSB} + tk_{PHA-AN}} +$$
$$k_{NB-NSB}^2 k_{PHA-AN} e^{tk_{NB-NSB} + tk_{NSB-PHA} + tk_{PHA-AN}} -$$
$$k_{NSB-PHA}^2 k_{PHA-AN} e^{tk_{NSB-PHA} + tk_{PHA-AN}} +$$
$$k_{NSB-PHA}^2 k_{PHA-AN} e^{tk_{NB-NSB} + tk_{NSB-PHA} + tk_{PHA-AN}} -$$
$$k_{NB-NSB} k_{PHA-AN}^2 e^{tk_{NB-NSB} + tk_{PHA-AN}} +$$
$$k_{NB-NSB} k_{PHA-AN}^2 e^{tk_{NB-NSB} + tk_{NSB-PHA} + tk_{PHA-AN}} +$$
$$k_{NSB-PHA} k_{PHA-AN}^2 e^{tk_{NSB-PHA} + tk_{PHA-AN}} -$$
$$k_{NSB-PHA} k_{PHA-AN}^2 e^{tk_{NB-NSB} + tk_{NSB-PHA} + tk_{PHA-AN}})) /$$
$$((k_{NB-NSB} - k_{NSB-PHA}) \times$$
$$(k_{NB-NSB} - k_{NSB-PHA})(k_{NSB-PHA} - k_{PHA-AN}))$$

A global fitting analysis was performed with the GC data for NB, PHA, and AN using Origin 9.0 for the values of (NB)0, kNB-NSB, kNSB-PHA, kPHA-AN. The fit did not converge when a similar analysis was performed for only 2 sequential reactions instead of 3. Once the forward rates and the initial concentration were derived, the set of differential equations was symbolically solved for 1 irreversible followed by 2 reversible reactions and also in the case where the irreversible reaction was in the middle (symbolic equations not shown due to space considerations). The rates for both are given in Table 2.

TABLE 2

Best fit to GC data for reverse rates in kinetic model. Forward rates are kept constant.

| Kinetic Model | $k_{NB-NSB}$ | $k_{NSB-PHA}$ | $k_{PHA-AN}$ | $k_{NSB-NB}$ | $k_{PHA-NSB}$ | $k_{AN-PHA}$ |
|---|---|---|---|---|---|---|
| 1 irrev, 2 rev | 0.0312 | 0.0107 | 0.0552 | — | 0.002 | 0.009 |
| 1 rev, 1 irrev, 1 rev | 0.0312 | 0.0107 | 0.0552 | 0.000 | — | 0.012 |

Example 2

Results

Studies of the mechanism for the electrochemical reduction of NB to AN (without a catalyst) demonstrate that in an acidic or neutral protic solution, such as water or methanol, NB undergoes two successive one-electron reductions in the presence of two protons to produce nitrosobenzene (NSB) and water (Equation 2a). The NSB then undergoes a second two-electron transfer step to form PHA (Equation 2b), which reacts with a further two protons and two electrons to form AN and water (Equation 2c). The overall reaction for NB reduction to AN thus requires 6 electrons and 6 protons (Equation 2d).

$$C_6H_5-NO_2 + 2e^- + 2H^+ \rightarrow C_6H_5-NO + H_2O \quad \text{(Equation 2a)}$$

$$C_5H_5-NO + 2e^- + 2H^+ \rightarrow C_5H_5-NHOH \quad \text{(Equation 2b)}$$

$$+C_6H_5-NHOH + 2e^- + 2H^+ \rightarrow C_6H_5-NH_2 + H_2O \quad \text{(Equation 2c)}$$

$$C_6H_5-NO_2 + 6e^- + 6H^+ \rightarrow C_6H_5-NH_2 + 2H_2O \quad \text{(Equation 2d)}$$

FIG. 1 shows the mechanism and electrochemical potentials for the photocatalytic reduction of NB to AN by CdS QDs (refs. A9-11; incorporated by reference in their entireties); although the present invention is not limited to any particular mechanism of action and an understanding of the mechanism of action is not necessary to practice the present invention. The potential is −0.159 V vs NHE for the first proton-coupled two-electron transfer step (NB to NSB) and +0.291 V vs NHE for the second two-electron transfer step (NSB to PHA) (ref. A11; incorporated by reference in its entirety). Cyclic voltammetry measurements demonstrate that once the NSB forms, it immediately proceeds to PHA and the whole process is detected as a single 4-electron transfer step (ref. A11; incorporated by reference in its entirety). At −0.459 V vs NHE, a final two-electron transfer step occurs to produce AN (ref. A11; incorporated by reference in its entirety). The energy of the conduction band-edge orbital of CdS QDs, measured either using cyclic voltammetry (ref. A12; incorporated by reference in its entirety) or a combination of ultraviolet photoemission spectroscopy and ground state absorption spectroscopy (ref. A13; incorporated by reference in its entirety), is high enough such that an electron photoexcited into this orbital has a enough reducing power to drive each step of the NB reduction to AN. 3-mercaptopropionic acid (3-MPA) was utilized as both a hole scavenger to regenerate the ground state of the QD, and as the primary proton donor: for each 2-electron, 2-proton step, two MPA molecules are oxidized and deprotonated to form a disulfide that is detectable via $^1$H-NMR (FIG. 5).

Figure 2A:
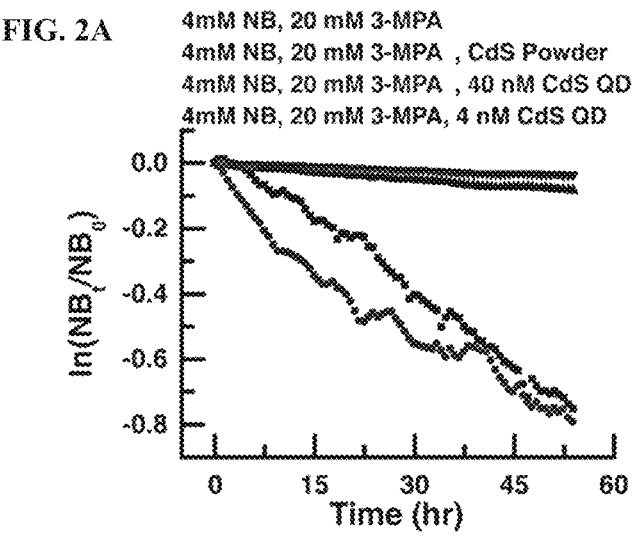
FIGS. 2A-C. (A) The time-dependent concentration of nitrobenzene (NB), obtained from integrated GC spectra, within samples of 4 mM nitrobenzene and 20 mM 3-MPA (top), or 4 mM NB and 20 mM 3-MPA and 5 µg CdS powder (upper), or 4 mM NB and 20 mM 3-MPA and 40 nM CdS QDs (bottom), or 4 mM NB and 20 mM 3-MPA and 4 nM CdS QDs (lower). All solutions are in an 80:20 (v:v) mixture of H2O:CH3OH. The samples are purged with argon and illuminated with a 7 mW 405 nm laser while stirring. The NB concentration is calculated by integrating the parent mass of NB, m/z 123, and normalizing to the integrated intensity of an ethyl ether standard. (B) $^1$H-NMR spectra of 4 mM NB and 16 mM 3-MPA in 80:20 D2O:D3OD, with and without 40 nM CdS QDs, before and after 7 hours of illumination with a 405 nm, 30 mW diode laser while stirring. Peaks are attributed to phenyl ring protons in NB, PHA and AN are indicated. Samples were purged with argon and allowed to sit for 30 minutes before the 0-hr spectra were taken. (C) The time-dependent concentration of NB (initially 4 mM) and reduction products PHA and AN in the presence of 20 mM 3-MPA and 4 nM CdS QDs. The concentration data (represented as points) is fit to a kinetic model of 3 sequential reactions (represented by lines). The NB concentration is measured as in (A) and the concentrations of the products are determined by deconvoluting the integrated product peak into corresponding contributions from AN and PHA.

FIG. 2A shows that NB in the presence of 3-MPA and CdS QDs degrades upon illumination with 405 nm light as detected by Gas-Chromatography Mass Spectrometry (GC-MS). These samples were prepared by adding 4 mM NB and 20 mM 3-MPA to a 4 nM solution of CdS QDs in 20:80 CH3OH:H2O, and purging the solution for 3 minutes with Ar(g). The samples are progressively illuminated with a 405 nm, 7.0 mW laser pointer while stirring. An autosampler injects the sample into the column which is then linearly heated. NB desorbs from the column at 210° C., in agreement with its boiling point. The concentration of NB was determined by integrating the GC peak at m/z=123 and comparing it to the peak for a known NB standard. In the presence of 4 nM CdS QDs and 20 mM 3-MPA, the NB concentration decays as a function of illumination time with approximate pseudo-first order kinetics and a rate constant of $-1.2 \times 10^{-2}$ hr$^{-1}$. Without QDs, there is some inefficient reduction of NB likely caused by the H$^+$ catalyzed photo-oxidation of 3-MPA14, with a rate constant of $-6.6 \times 10^{-4}$ hr$^{-1}$. The 4 nM CdS QD catalyst increases the rate constant of NB reduction by a factor of 18.5 under these conditions. The CdS QD catalyst degrades NB a factor of 12.6 faster than a CdS powder. Increasing the concentration of QDs from 4 nM to 40 nM while keeping the initial concentration of NB the same increases the initial decay rate constant by a factor of 3.4 (to $-2.8 \times 10^{-2}$ hr$^{-1}$), but does not increase the average reduction rate constant over 55 hr.

Figure 2B:
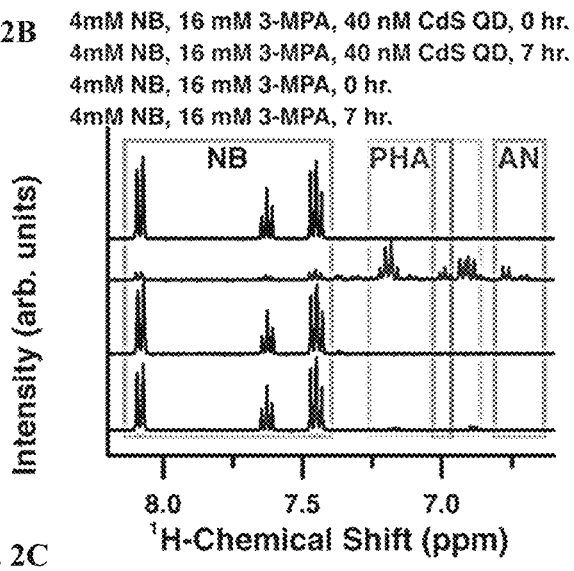

$^1$H NMR spectra of the illuminated reaction mixtures show that photo-reduction of NB forms AN through a PHA intermediate (FIG. 2B). The NMR does not detect any NSB in these samples; this result agrees with cyclic voltammetry measurements that indicate that NSB is a relatively short-lived species (ref. A11; incorporated by reference in its entirety). Integration of the peaks demonstrates that, the total intensity of phenyl ring protons in these reaction mixtures is conserved during the photoreaction.

Figure 2C:
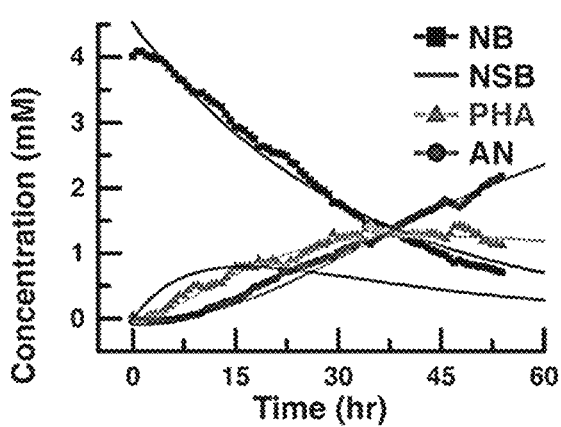

FIG. 2C shows the time dependence of the photodegradation of NB and the formation of PHA and AN photoproducts. During the first ~5 hours of illumination, PHA is the majority product and the concentration of AN is below 10 µM. As the reaction proceeds and PHA reaches a maximum steady state concentration of 1.4 mM, the AN concentration increases linearly. After 38 hours of illumination, the concentration of NB falls to 15% of its initial value. These data were fit to a kinetic model of three sequential reactions (Equation 3); the second reaction is irreversible to account for the observation that no NSB is observed in the steady state.

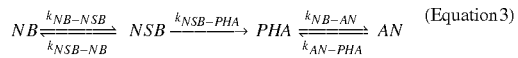 (Equation 3)

The kinetic model was globally fit to the GC concentration data for NB, PHA, and AN as a function of time to derive kinetic rate constants for each step. The analysis supports a higher forward rate constant for NSB to PHA (kNB-NSB=0.0312 hr-1) and PHA to AN (kPHA-AN=0.0552 hr-1) than the NSB-PHA (kNSB-PHA=0.0107 hr-1) step. The back reaction kAN-PHA is 0.013 hr-1 and kNSB-NB is 0.000 hr-1. An essentially identical fit is achieved by asserting that the NB-to-NSB reaction is the irreversible one, that is kNSB-NB~0 (Table 2). Although NSB was not directly detected, the model indicates that the concentration of NSB peaks after ~10 hr and decreases which is due to the NB being used up in this batch reactor-type setup. The concentration of PHA, which is formed from NSB, peaks at ~33 hr and then decreases as the availably of NSB decreases. The concentration of AN and PHA after 54 hours of illumination was calculated to determine that each QD reduces 825,000 NB molecules to produce 500,000 AN and 325,000 PHA molecules. This degree of reduction corresponds to an average of 4.5 million electrons transferred from each QD to NB, NSB and PHA.

Figure 3:
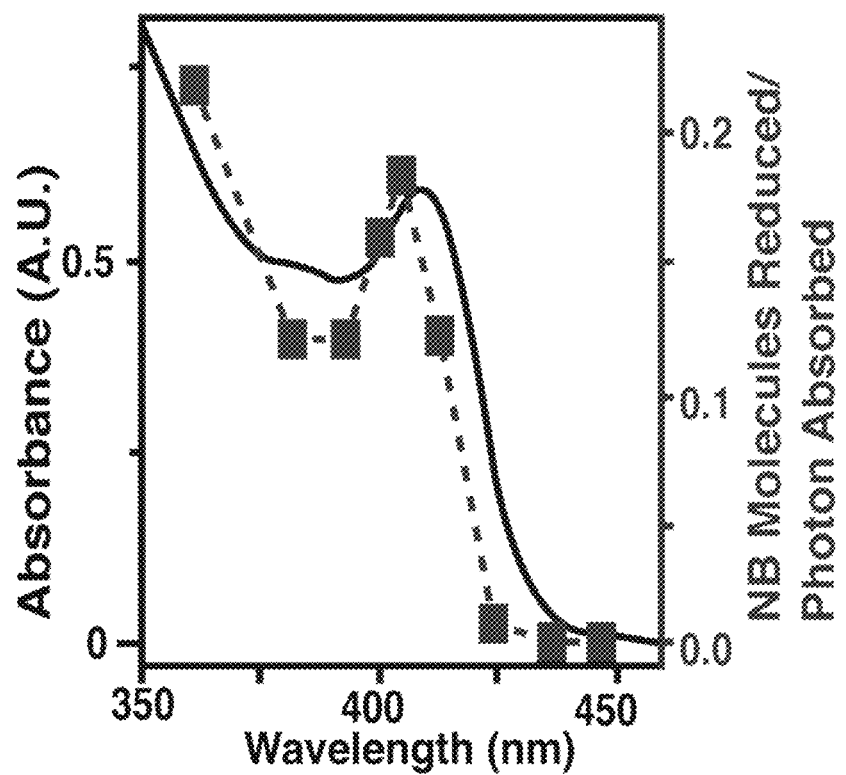
FIG. 3. The excitation wavelength-dependent photo-activity of CdS QDs for the reduction of NB to AN (right axis, dashed line and squares) overlayed with the QD's measured absorption spectrum (left axis, solid line). To obtain the action spectrum, nine reaction mixtures of 4.0 µM CdS QDs and 0.4 mM NB in a 80:20 water:methanol mixture were illuminated for four minutes by a ~1-mW laser tuned to each wavelength. The $^1$H-NMR spectra of the illuminated samples were compared to those of a control kept in the dark, to determine the concentration of NB that was photoreduced. All samples had a volume of 1.0 mL and were degassed by bubbling with argon for four minutes each. The number of photons absorbed during the entire 4-minute illumination at each wavelength was calculated from ground state extinction spectrum of the QDs and the path-length of the GC-MS vial.

FIG. 3 shows that the CdS QDs are the active chromophores for photocatalysis in this system. It is a plot of the quantum yield of NB photoreduction (number of NB molecules reduced per photon absorbed by the sample) vs. excitation. This action spectrum overlays the ground state absorption spectrum of the QDs. To produce the action spectrum, ten identical vials were prepared with 4 mM NB, 20 mM 3-MPA, and 4.0 µM CdS QDs, and each sample was illuminated at one of nine wavelengths between 361 nm and 448 nm centered around the first absorption peak of the QDs (415 nm). The lowest energy transition for NB itself is an n to π* transition that occurs at 340 nm (ref. A15; incorporated by reference in its entirety), so the NB we is not directly excited by this range of wavelengths.

Figure 4A:
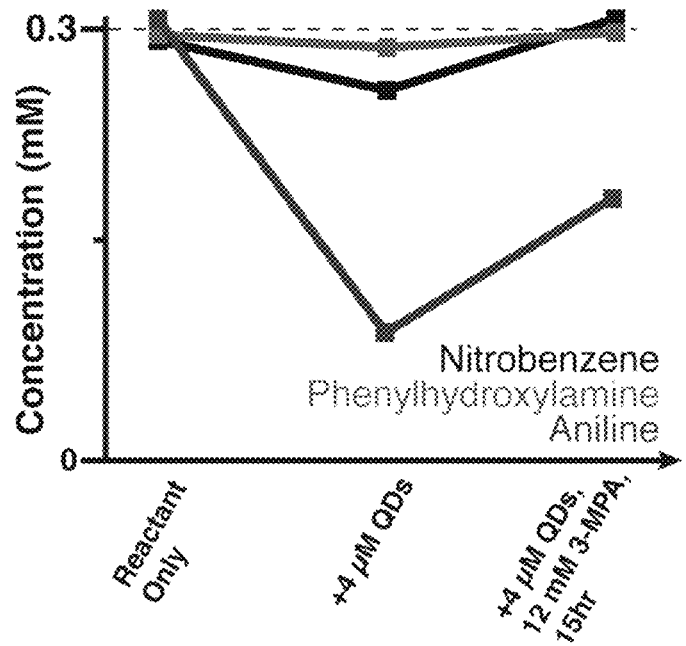
FIGS. 4A and 4B. (A) The apparent concentrations, measured by NMR, of NB (middle) PHA (top), and AN (bottom) in a 0.3 mM solution of each molecule in an 80:20 CD3OD:D2O mixture, after: (i) the addition of 4 µM CdS QDs, stirring for 5 min and resting for 30 min, and (ii) the addition of 4 µM CdS QDs and 12 mM 3-MPA and waiting 15 hr unstirred in the NMR tube. (B) The apparent concentrations, measured by NMR, of NB (bottom), PHA (middle) and AN (top) in in an 80:20 D3OD:D2O solution (1 mL) of initially 0.3 mM NB (no added PHA or AN) after: (i) the addition of 4 µM CdS QDs, stirring for 5 min and resting for 30 min, (ii) the addition of 4 µM CdS QDs and illumination at 405 nm for 10 minutes (33.0 mW laser) while stirring, and (iii) the addition of 4 µM CdS QDs, illumination at 405 nm for 10 minutes while stirring, post-illumination addition of 12 mM 3-MPA, and waiting 15 hr. The apparent total concentration of aromatic molecules is not 0.3 mM in cases where some molecules are adsorbed to the surfaces of the QDs and are therefore "NMR-invisible".
Figure 6:
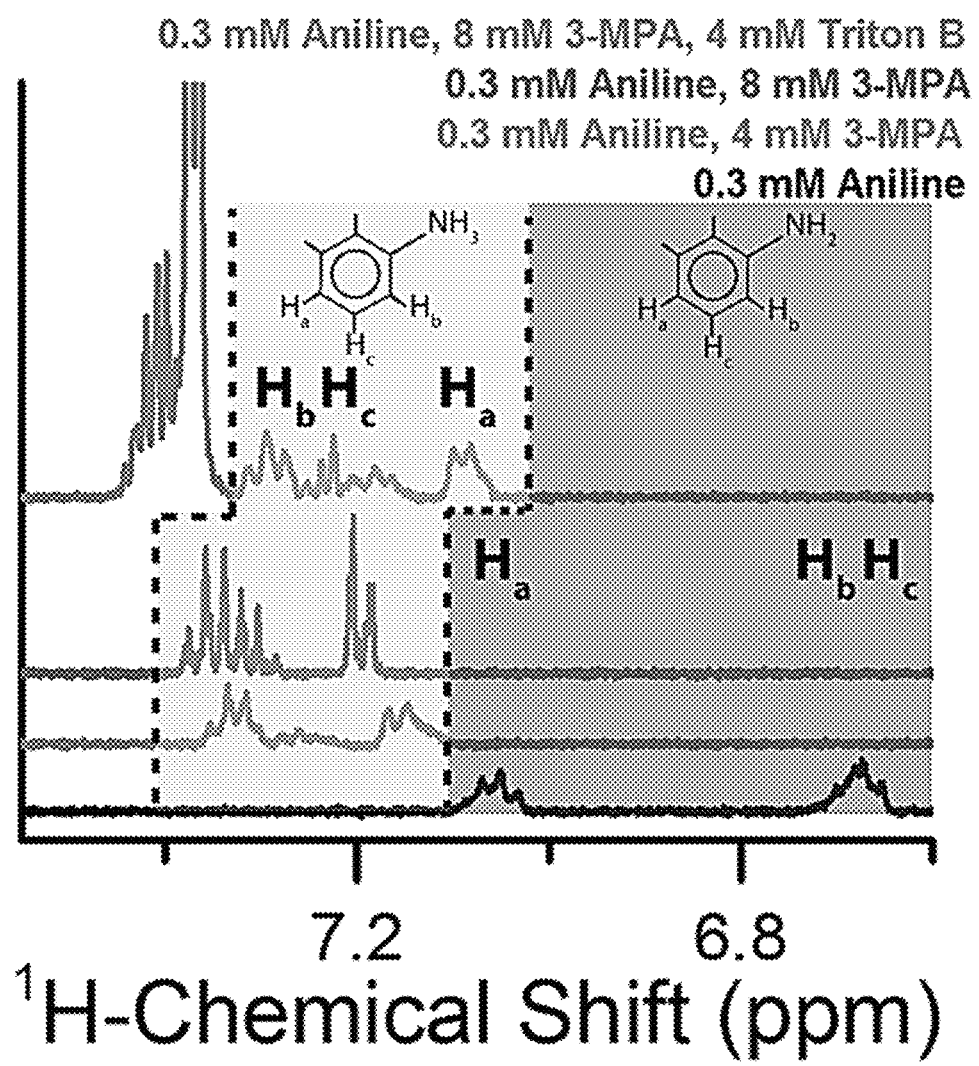
FIG. 6. Aromatic regions of the 1H-NMR spectra of 0.3 mM aniline (bottom) after the sequential addition of 4 mM 3-MPA (lower), 8 mM 3-MPA (upper), and 4 mM Triton B (top). The peaks corresponding to the aromatic protons of aniline shift downfield and broadens when the molecule is protonated to the anilinium ion in the presence of 8 mM 3-MPA at pH 4.6. The addition of Triton B upfield shifts the protons.
Figure 7A:
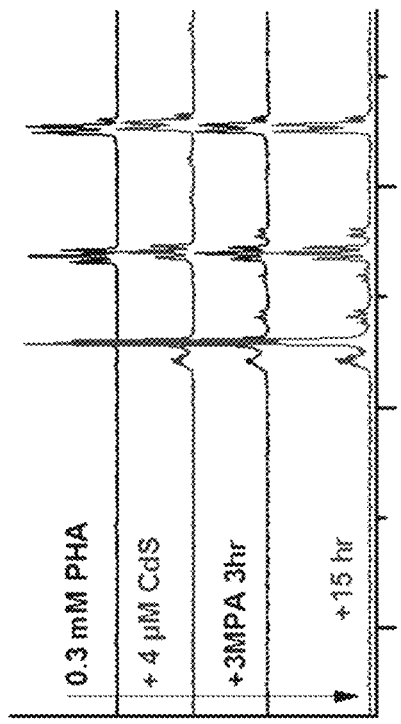
FIGS. 7A-D. $^1$H-NMR spectra of nitrobenzene (A), aniline (B), or phenylhydroxylamine (C) and 3-MPA CdS QDs. A 0.3 mM solution of the free molecule (top) is first analyzed and compared to an identical solution with 4 µM CdS QDs (upper). 8 mM 3-MPA is added to each QD solution and they are allowed to equilibrate for three hours before taking an NMR spectrum (lower). The same samples are then analyzed 15 hr later to ensure that displacement has progressed to the fullest extent (bottom). (D) $^1$H-NMR spectra of 0.3 mM solution of nitrobenzene and 4 µM CdS QDs (top). The solution is illuminated with a 33.0 mW 405 nm laser diode for 10 min (upper). 8 mM 3-MPA is added to the solution and allowed to equilibrate for three hours before taking an NMR spectrum (lower). The same sample is analyzed 15 hr later to ensure that displacement has progressed to the fullest extent possible (bottom).
Figure 7B:
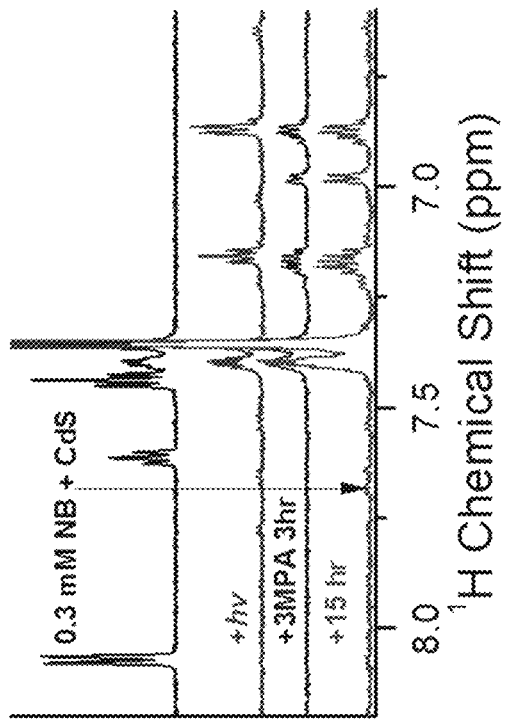
Figure 7C:
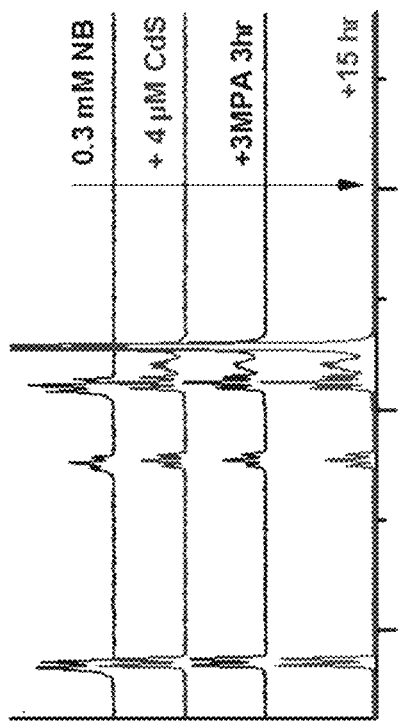
Figure 7D:
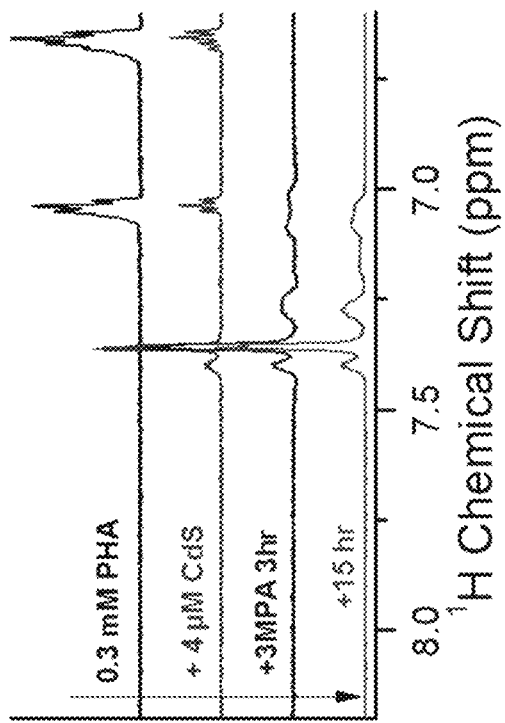

At neutral pH, AN desorption from the CdS QDs is a rate limiting step for catalytic turnover. FIG. 4A shows the integrated NMR signal from NB, PHA, and AN within 0.3 mM solutions of each molecule in a 20:80 mixture of D3OD:D2O. After addition of 4 µM CdS QDs, the apparent concentrations of NB, PHA, and AN decrease by 5%, 14% and 71%, respectively, because the molecules bind to the QDs (Table 1). The relatively large decrease from the initial concentration of AN is expected, as (i) AN is known to chemisorb to QDs via its amine group, while NB and PHA probably physisorbs to the QDs, and (ii) AN is less soluble in the water/methanol mixture than NB or PHA. Addition of 12 mM 3-MPA desorbs all of the NB and PHA from the QDs through displacement, and increases the free concentration of AN from 30% to 61% of the aniline signal prior to QD addition. The increase is due to the protonation of the aniline to anilinium which has a higher solubility than aniline in water and can be seen in 1H-NMR (FIG. 6).

TABLE 1

Apparent concentration of nitrobenzene, phenylhydroxylamine, aniline as calculated from $^1$H-NMR in the presence of QDs and excess 3-MPA.

| Concentration (µM) | Nitro-benzene | Phenyl-hydroxylamine | Aniline | Total Free |
|---|---|---|---|---|
| Nitrobenzene Only | 300.0 | — | — | 300.0 |
| Nitrobenzene, CdS | 255.0 | — | — | 255.0 |
| 3MPA, Nitrobenzene, CdS | 269.6 | — | — | 269.6 |
| 3MPA, Nirobenzene, CdS, 15 hr | 306.9 | — | — | 306.9 |
| Phenylhydroxylamine Only | — | 280.5 | 19.5 | 300.0 |
| Phenylhydroxylamine, CdS | — | 239.1 | 53.6 | 292.7 |
| 3MPA, Phenylhydroxylamine, CdS | — | 223.0 | 54.2 | 277.2 |

TABLE 1-continued

Apparent concentration of nitrobenzene, phenylhydroxylamine, aniline as calculated from $^1$H-NMR in the presence of QDs and excess 3-MPA.

| Concentration (μM) | Nitro-benzene | Phenyl-hydroxylamine | Aniline | Total Free |
|---|---|---|---|---|
| 3MPA, Phenylhydroxylamine, CdS, 15 hr | | 247.1 | 62.9 | 309.9 |
| Aniline Only | — | — | 300.0 | 300.0 |
| Aniline, CdS | — | — | 77.1 | 77.1 |
| 3MPA, Aniline, CdS | — | — | 129.9 | 129.9 |
| 3MPA, Aniline, CdS, 15 hr | | | 173.0 | 173.0 |
| Nitrobenzene, CdS, 0 min. | 242.1 | — | — | 242.1 |
| Nitrobenzene, CdS, 405 nm 10 min. | 10.4 | 152.9 | 56.7 | 220.1 |
| 3MPA, Nitrobenzene, CdS, 405 nm 10 min. | 13.2 | 92.8 | 110.9 | 216.9 |
| 3MPA, Nitrobenzene, CdS, 405 nm 10 min, 15 hr | 5.2 | 139.6 | 159.2 | 304.0 |

Figure 4B:
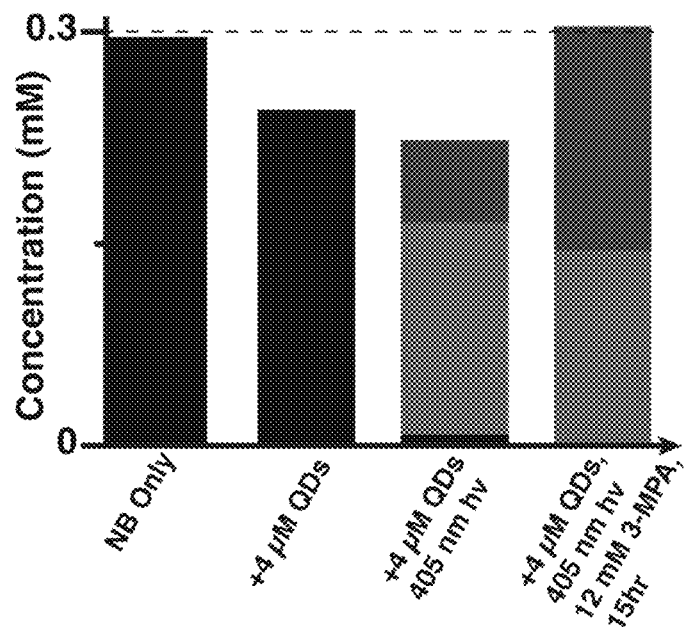

Illumination of the NB-QD mixture for 10 minutes at 405 nM (33.0 mW) decomposes 97% of the NB to form PHA (70%) and AN (27%), but the total concentration of unbound phenyl ring protons in this sample is only 70% of the original total (FIG. 4B). All of the photoproducts were recovered by adding 12 mM 3-MPA and waiting 15 hr. The final composition of the mixture is 46% PHA and 52% AN. In agreement with the GC-MS study, no other products, such as NSB, azobenzene or 1,2-diphenylhydrazine, were detected.

These experiments demonstrate that, in a methanol/water solution in the absence of 3-MPA, the number of bound molecules is quantifiable by observing the decrease in signal of each molecular species. Molecules bound to nanoparticles have a large rotational correlation time, which broadens the NMR resonance for protons close to the QD and makes it difficult to distinguish from the baseline noise (refs. A16-19; incorporated by reference in their entireties). The degree of broadening is proportional to the fraction of time that the molecules are adsorbed to the QD as well as the size and rigidity of the molecule itself. Broadening of the $^1$H-NMR signals from NB, PHA, or AN was not observed, which indicates a longer residence time on the QD. The fact that bound molecules are not observable in the NMR was utilized to calculate the number of AN bound per QD. QDs were added to a solution of AN, and it was observed that 52 AN molecules bind per QD. AN therefore acts as a poison for the QD catalyst under neutral pH conditions, and thus AN desorption is a rate limiting step for NB reduction. The addition of 3-MPA lowers the pH of the solution below the pKa of aniline (pKa=4.87), which protonates it to anilinium and makes it more soluble in a protic solvent (FIG. 6-7). 3-MPA also aids in the displacement of the bound aniline species from the surface of the QD. 8 mM 3-MPA does not quantitatively displace all bound AN from the QDs in the AN only sample, when compared to the photoilluminated NB sample however, both displace the same amount of AN since in the latter case, AN represents half of the generated photoproducts. PHA has a higher solubility in a protic solvent than AN due to its alcohol group and thus its ability to desorb from the QD is not strongly pH or 3-MPA dependent.

Example 3

Photocatalytic Reduction of Nitrobenzene to Aniline by CdS QDs

The multistep reduction of NB to AN utilizes a total of six electrons and protons and occurs through NSB and PHA intermediates. In a 1:1 H2O:MeOH mixture, the potential for the 2e$^-$, 2H$^+$ reduction of NB to NSB, with elimination of water, is −0.16 V vs NHE), the potential for the 2e$^-$, 2H$^+$ reduction of NSB to PHA is +0.29 V vs NHE, and the potential for the 2e$^-$, 2H$^+$ reduction of PHA to AN, with elimination of water, is −0.46 V vs NHE (ref. B60; incorporated by reference in its entirety). Since the formation of each 2e$^-$ intermediate is detected electrochemically as a concerted two-electron step (with a single current peak for each step), the 2e$^-$, 2H$^+$ reduction potentials were equated with the 1e$^-$, 1H$^+$ reduction potentials. All of these potentials are lower than that of electrons in the LUMO (lowest state of the conduction band) of a 4.5 nm CdS QD, the potential of which has been measured to be as high as −2.0 V vs NHE (ref. B64; incorporated by reference in its entirety). The electron transfer to each substrate therefore occurs spontaneously upon photoexcitation of the QD. The NSB intermediate is easier to reduce than NB, so without trapping by a nucleophile, NSB is typically not observed, and the reaction of NB to PHA is detected as a single four-electron transfer step (ref. 52, 60, 65; incorporated by reference in their entireties).

Figure 8:
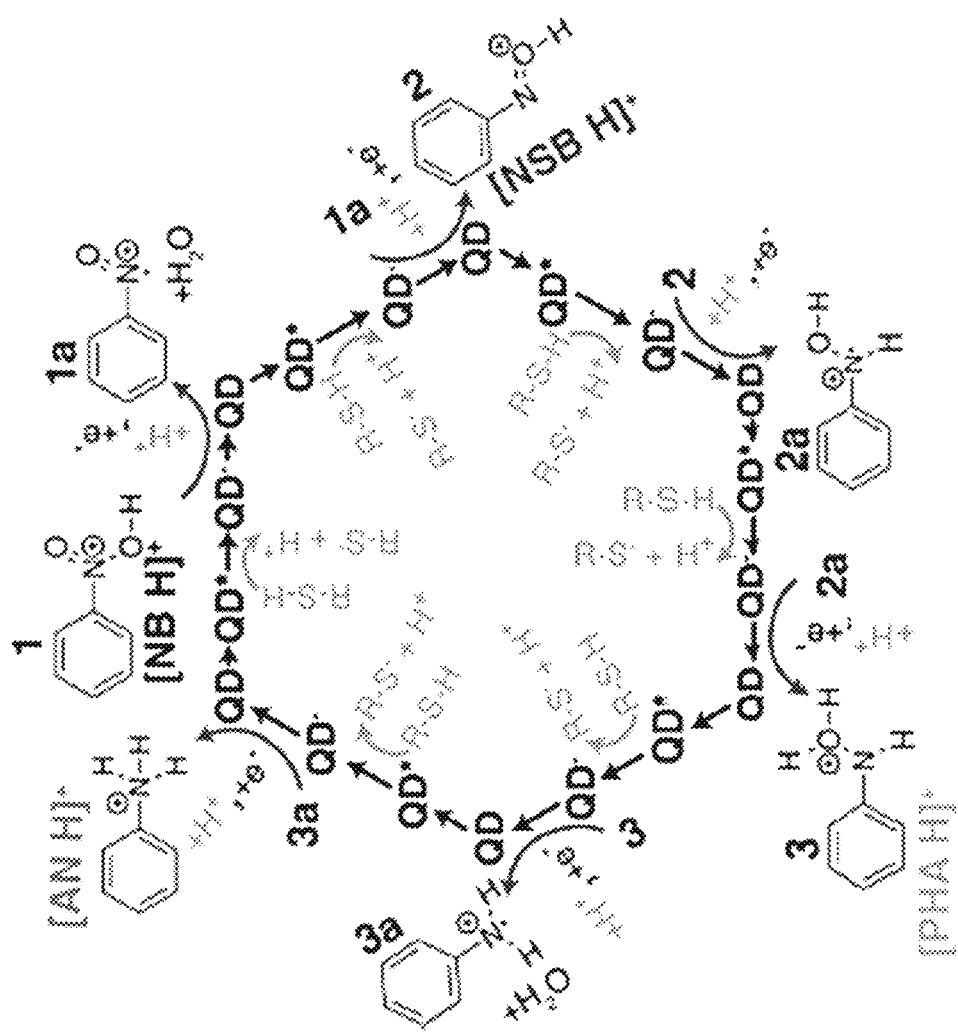
FIG. 8. catalytic cycle for the six-electron, six-proton photoreduction of nitrobenzene (NB, 1) to aniline (AN) through nitrosobenzene (NSB, 2) and phenylhydroxylamine (PHA, 3) two-electron intermediates, all of which are partially protonated at ph 3.6. a3-Mercaptopropionic acid (R—S—H) serves as a sacrificial reductant to regenerate the CdS QD catalyst, but it cannot account for all of the protons and electrons used in the reaction, some of which are provided by the MeOH co-solvent. 1a, 2a, and 3a denote proposed one-electron intermediates formed during the cycle.

The photocatalytic cycle from NB to AN under acidic conditions is outlined in FIG. 8. For clarity, the protonated forms of all reagents and products are shown, but at pH of 3.6, mixtures of protonated and unprotonated NB, NSB, PHA, and AN are present.

Unlike other published mechanisms, the cycle in FIG. 8 includes plausible one-electron intermediates that are not observed in the electrocatalysis experiment. These intermediates are included because, given the flux of photons into the system (4.6×10$^{17}$ photons cm$^{-2}$ s$^{-1}$), the absorption coefficient of the QDs (which dictates that they absorb 1.1% of incident photons), and the excited state lifetime of the QDs without added NB, each QD contains one exciton or fewer at any given time and, therefore, only delivers one electron at a time. Furthermore, this photon flux dictates that the lifetime of each one-electron intermediate shown in FIG. 8 must be at least 7.1 ms such that it can be converted, upon creation of the next exciton in the QD, to the two-electron product.

Example 4

Analysis of the Adsorption of Reagents and Photoproducts to the Surface of QDs In order to determine whether the reactions in the cycle depicted in FIG. 8 occur within temporary encounter complexes of freely diffusing QDs and molecules or whether the molecules are statically adsorbed to the QDs, the number of NB, NSB, PHA, and AN molecules that adsorb to each QD under acidic conditions (pH ~5) were measured, by NMR. Molecules bound to nanoparticles have a large rotational correlation time, which broadens the NMR resonance for protons close to the QD and makes it difficult to distinguish the signal from the baseline noise. The degree of broadening scales with the fraction of time that the molecule is adsorbed to the QD, as well as the size and rigidity of the molecule. If the broadening upon adsorption is dramatic enough, the molecules become NMR-invisible (refs. 51, 66-68; incorporated by reference in their entireties). One can therefore estimate the number of bound molecules per QD by monitoring the decrease in the integrations of their NMR signals upon mixing them with QDs. Table 3 lists the average number of NB, NSB, PHA, and AN molecules bound per QD in mixtures of 0.4 mM of each of the molecules with 4.0

μM QDs (where the molecules were added directly, not produced by reaction of NB) and the corresponding adsorption constants. NMR spectra of these samples were acquired after 1 h of stirring in the dark. For comparison, also listed is the data for samples without excess MPA (pH ~9.0 due to the presence of Triton B), at which pH the unprotonated forms of NB, NSB, PHA, and AN dominate.

TABLE 3

Number of Bound Molecules per QD as a Function of MPA Concentration

| | No MPA (pH ~9) | | 15 nM MPA (pH ~5) | |
|---|---|---|---|---|
| | Molecules bound per QD | $K_{ads}$ = [bound]/[free] | Molecules bound per QD | $K_{ads}$ = [bound]/[free] |
| NB | 80.5 ± 8.9 | 0.81 ± 0.09 | 80.3 ± 1.2 | 0.80 ± 0.01 |
| NSB | 41.3 ± 2.2 | 0.41 ± 0.02 | 77.9 ± 2.7 | 0.78 ± 0.03 |
| PHA | 79.3 ± 1.6 | 0.79 ± 0.02 | 72.0 ± 5.5 | 0.72 ± 0.05 |
| AN | 82.1 ± 2.2 | 0.82 ± 0.02 | 13.5 ± 2.4 | 0.13 ± 0.02 |

Measured by 1H NMR on samples comprising 0.4 mM of each molecule with 4.0 μM QDs and stirred for 1 h before measurement From the data in Table 3, it is concluded that protonation does not affect the binding constant of NB (pKa ~4.0), but it decreases the binding constant of AN (pKa ~4.6) by approximately a factor of 6, probably because of a large increase in the solubility of AN in water once protonated (ref. 61; incorporated by reference in its entirety). In going from pH 9 to pH 5, The number of protonated PHA molecules (pKa ~1.9) is only changed from 0.1% to 4.7%; the average solubility or affinity for the QD surface is not significantly affected. The binding constant of the QD-NSB complex increases by approximately a factor of 2 on going from <1% protonated NSB at pH 9 to 14% protonated NSB at pH 5. The binding constant of a QD-molecule complex depends on a number of factors, including the solubility of the molecule in the surrounding solvent and the magnitude of electrostatic and van der Waals interactions with the QD core and the ligand shell. Given that the maximum number of molecules that adsorb to the QDs (under the two pH values examined) is ~80 for all four molecules, it can be concluded that there exist approximately 80 binding sites for molecules of this size on the surface of the QD. Furthermore, the fact that ~80 NB, NSB, and PHA molecules are bound at acidic pH implies that under the conditions used to gather the data in FIG. 2, there is no incentive for the catalytic substrate to desorb from the QD surface until AN is formed, indicating that all steps in the catalytic cycle occur through "static" proton-coupled electron transfer reactions from QDs to preadsorbed molecules and are not diffusion controlled. These data also indicate one reason why, when excess MPA is not present, the number of catalytic turnovers (over 54 h) decreases by a factor of ~2; under neutral or basic conditions, AN saturates the QD surface and leaves no room for NB to adsorb and thereby poisons the catalyst.

Example 5

Measurement of the Rates of Some Elementary Electron and Hole Transfer Steps

Figure 9A:
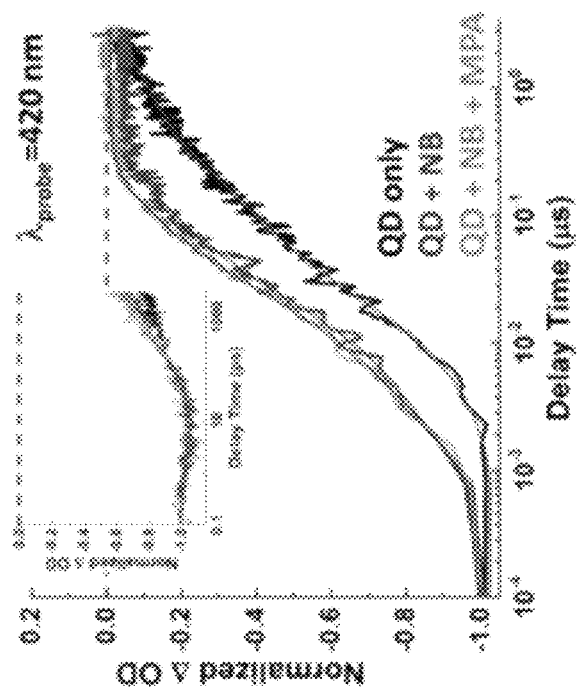
FIGS. 9A-D. (A) Visible TA spectrum of 2 µM CdS QDs (no added NB or excess MPA) in 80:20 H2O:MeOH, collected 1 ns after excitation at 390 nm. Inset: Near-infrared TA spectrum of the same sample of CdS QDs collected 1 ps after excitation at 390 nm. The vertical dotted lines mark two of the wavelengths at which we monitored the dynamics of the excited state of the QD, as shown in parts B-D. (B) Normalized kinetic traces, monitored on the nanosecond-tomicrosecond time scale, extracted at 420 nm from the TA spectra of the 2 μM QDs, the QDs with 1000 eq of NB, and the QDs with 1000 eq of NB and 1000 eq of 3-MPA. Inset: Normalized kinetic traces extracted at 420 nm from the TA spectra of the same samples, but monitored on the ultrafast time scale (150 fs–3 ns). Signals at 420 nm are dominated by the dynamics of the excitonic electron. (C) Normalized kinetic traces, monitored on the ultrafast time scale, extracted at 1250 nm from the TA spectra of the same samples as in part B. Signals at 1250 nm are dominated by the dynamics of the excitonic hole. (D) Normalized kinetic traces, monitored on the nanosecond-to-microsecond time scale, extracted at 420 nm from the TA spectra of the QDs, the QDs with 1000 eq of NB and 1000 eq of 3-MPA, the QDs with 1000 eq of NSB and 1000 eq of 3-MPA, and the QDs with 1000 eq of PHA and 1000 eq of 3-MPA.

FIG. 9A shows the transient absorption (TA) spectrum of a sample of 2 μM CdS QDs (no added NB or excess MPA) in 80:20 H2O:MeOH, collected 1 ns after excitation at 390 nm. The main feature in this spectrum is the bleach of the ground-state absorption centered at 413 nm. This bleach reflects the depopulation of the ground state by the 390 nm pump laser. It forms on the time scale of photon absorption and recovers as the excitonic electron leaves the conduction band of the QD core, here by electron transfer to NB, NSB, or PHA. Electron dynamics were monitored at 420 nm (marked with a dotted line), rather than the center of the bleach, because, at shorter wavelengths, scatter from the pump laser contaminates the signal. The ground-state bleach signal of cadmium chalcogenide QDs is not sensitive to the location or dynamics of the excitonic hole because of the high near-degeneracy of valence band-edge states compared to conduction band-edge states (refs. 69-72; incorporated by reference in their entireties). The hole was instead monitored at 1250 nm (FIG. 3A, inset), where, for CdSe QDs, it is known that the dynamics of the TA signal are dominated by the dynamics of the excitonic hole (ref. 69; incorporated by reference in its entirety). Indeed, dynamics are observed at 1250 nm that are not observed at 420 nm; it is these dynamics that are attributed to the excitonic hole.

Figure 9B:
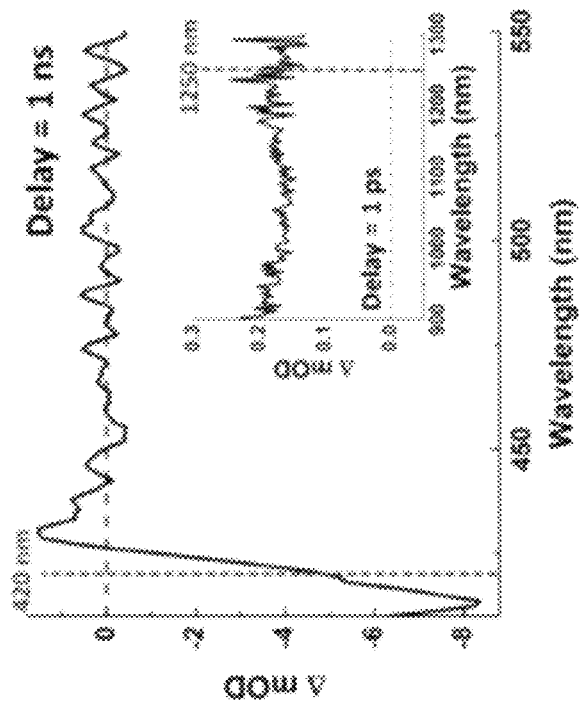

FIG. 9B shows the dynamics of the excitonic electron, monitored at 420 nm, for the QD, the QD plus 1000 equiv of NB, and the QD plus 1000 eq of both NB and MPA. The time scale focused on is 0.1 ns to 1 μs, because the TA signal at this wavelength does not begin to change until ~100 ps after photoexcitation (see FIG. 9B, inset), so the dynamics are more accurately monitored and fit on the nanosecond time scale. The kinetic traces in FIG. 3B were fit using a sum of simple exponential components convoluted with an instrument response function. The kinetic trace for the QD-only sample fits to a sum of three exponential components with time constants of 18 ns, 154 ns, and 1.6 μs ($\tau 5$, $\tau 6$, and $\tau 7$, respectively, in Table 4). On the basis of extensive previous work on exciton dynamics in cadmium chalcogenide QDs (refs. 69-72; incorporated by reference in their entireties) and the known dynamics specific to the excitonic electron, the 18 ns component was assigned to radiative recombination and the two longer components to recombination of the excitonic electron with a surface or lattice-trapped hole. When fitting the kinetic traces corresponding to the samples of QDs mixed with NB or NB and MPA, it was found that, in addition to the components needed to fit the kinetic trace for the QDs alone, a component with either $\tau=1.1$ ns (green) or $\tau=1.7$ ns (orange) is needed to adequately fit the kinetic trace (these time constants are listed as "$\tau 4$" in Table 4). This time constant is assigned in both cases to transfer of the photoexcited electron to NB.

TABLE 4

Time Constants for Excited-State Decay of CdS QDs with Various Photoxidants and the Photoreductant MPA[a]

| | $\tau_1^b$ fs ($A_1$) h+ trapping | $\tau_2^b$ ps ($A_2$) h+ transfer to MPA | $\tau_3^b$ ps ($A_3$) h+ trapping | $\tau_4^c$ ns ($A_4$) e− transfer to photo-oxidant | $\tau_5^c$ ns ($A_5$) radiative CR (e− + h+) | $\tau_6^c$ ns ($A_6$) CR of e− with trapped hole | $\tau_7^c$ μs ($A_7$) CR of e− with trapped hole |
|---|---|---|---|---|---|---|---|
| QD | 440 ± 32 (0.87) | — | 63 ± 10 (0.13) | — | 18 ± 1 (−0.45) | 154 ± 11 (−0.35) | 1.6 ± 0.1 (−0.20) |

TABLE 4-continued

Time Constants for Excited-State Decay of CdS QDs with Various Photoxidants and the Photoreductant MPA[a]

| | $\tau_1{}^b$ fs ($A_1$)<br>$h^+$ trapping | $\tau_2{}^b$ ps ($A_2$)<br>$h^+$ transfer to MPA | $\tau_3{}^b$ ps ($A_3$)<br>$h^+$ trapping | $\tau_4{}^c$ ns ($A_4$)<br>$e^-$ transfer to photo-oxidant | $\tau_5{}^c$ ns ($A_5$)<br>radiative CR ($e^- + h^+$) | $\tau_6{}^c$ ns ($A_6$)<br>CR of $e^-$ with trapped hole | $\tau_7{}^c$ μs ($A_7$)<br>CR of $e^-$ with trapped hole |
|---|---|---|---|---|---|---|---|
| QD-NB | 440 (0.84) | — | 63 (0.16) | 1.1 ± 0.5 (−0.33) | 18 (−0.36) | 101 ± 4 (−0.28) | offset[d] (−0.03) |
| QD-[NB H]$^+$ + MPA | 440 (0.71) | 5.7 ± 1.0 (0.17) | 63 (0.12) | 1.7 ± 0.3 (−0.31) | 18 (−0.37) | 82 ± 2 (−0.31) | offset[d] (−0.01) |
| QD-[NSB H]$^+$ + MPA | Not measured | Not measured | Not measured | 0.82 ± 0.94 (−0.44) | 18 (−0.28) | 208 ± 11 (−0.28) | offset[d] (0.002) |
| QD-[PHA H]$^+$ + MPA | Not measured | Not measured | Not measured | — | 18 (−0.39) | 406 ± 14 (−0.58) | offset[d] (−0.03) |

[a]Lifetimes in bold are those that are not found in the QD-only sample. Each lifetime is the average of two measurements on separately prepared samples that differed by less than 50%. The quantities in parentheses are the fractional amplitudes of each component at each probe wavelength: $A_1 + A_2 + A_3 = 1$ and $A_4 + A_5 + A_6 + A_7 = 1$.
[b]Monitored at $\lambda_{probe}$ = 1250 nm.
[c]Monitored at $\lambda_{probe}$ = 420 nm.
[d]Fit as a constant γ-offset rather than an exponential decay of the signal because the decay is too slow to measure on this time scale.

The slight discrepancy between the time constants for electron transfer from a photoexcited CdS QD to NB with excess MPA (1.7 ns) and without excess MPA (1.1 ns) could be due to the different protonation states of NB under those two conditions. Alternatively, it could be due to the fact that, when excess MPA is present, it scavenges the excitonic hole of the QD to form QD•—, which then is the electron donor to NB. When MPA is not present, the excited state of the QD, QD*, is the electron donor.

Figure 9D:
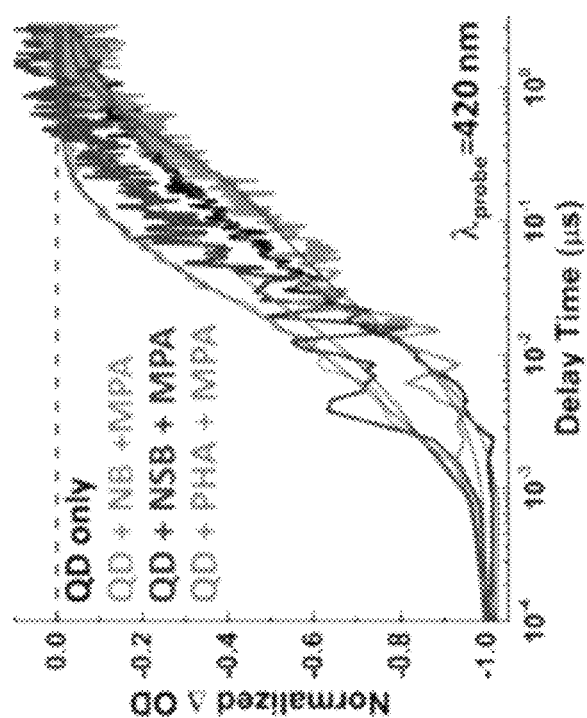
Figure 9C:
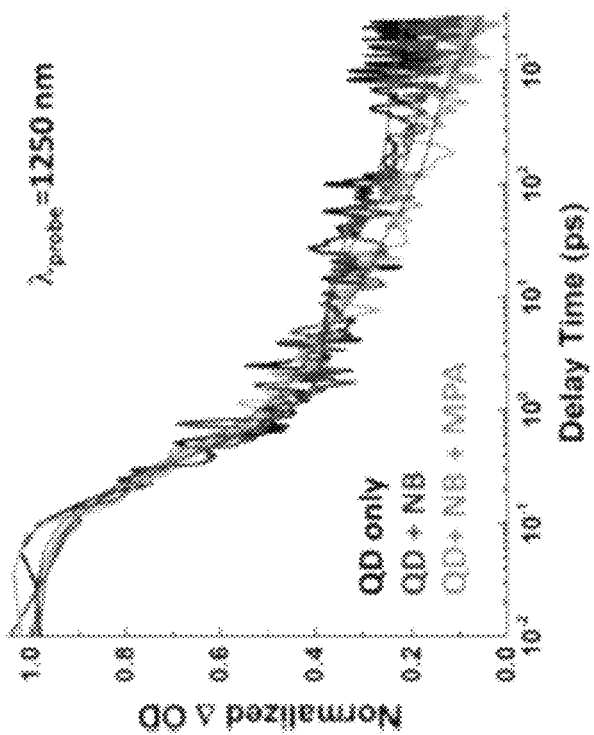

The dynamics of the hole transfer process were obtained from the dynamics in FIG. 9C, which shows kinetic traces extracted from the TA spectra of the same samples as in FIG. 9B, but monitored at 1250 nm. The dynamic components at 1250 nm attributable to photoinduced intraband transitions of the excitonic hole are those components that are not present in dynamics of the ground-state bleach. Fits to these kinetic traces show that hole transfer from a photoexcited CdS QD to MPA occurs in 5.7 ps (τ2 in Table 4), prior to the electron transfer process. This order of events is reflected in the catalytic cycle in FIG. 8. The 5.7 ps component adequately fits the kinetic trace for the sample of QDs plus NB and MPA, but it is not needed to fit the traces for the samples of QDs alone or QDs plus NB. Therefore it is the excess MPA in solution, not the MPA bound to the QD (which is present in all three samples), that is responsible for the hole scavenging. This indicates that the hole transfer process is not observed in the presence of MeOH without excess MPA because MeOH scavenges holes from surface traps on the QD surface, rather than holes from the QD core; the signal at 1250 nm is not sensitive to the dynamics of surface-trapped holes. The dynamics in FIG. 9C also show the presence of two other pathways with time constants of 440 fs and 63 ps. These processes are seen in all three samples (Table 4), have time constants that correspond to those observed for decay of excitons in CdSe QDs69 and are assigned to trapping of the hole to a lattice chalcogenide (<1 ps) and trapping of the hole to a surface chalcogenide (~50 ps).

FIG. 9D shows the same type of data as FIG. 9B, the dynamics of the photoexcited electron monitored at 420 nm, for a QD-only sample and for samples of QDs mixed with NB, NSB, or PHA. All samples have excess MPA, in order to best simulate the conditions of the catalysis. The time constant for electron transfer from the QD to [NSB H]$^+$(~0.8 ns) is shorter than that for electron transfer from the QD to [NB H]+(~1.7 ns). Both of these time constants are longer than most measured electron transfer time constants from CdS QDs to adsorbed acceptors (refs. 73-75; incorporated by reference in their entireties), but they are too short to reflect a diffusion-limited electron transfer process, which, based on the collision frequency, has a minimum value of 30 ns for this system. This result supports the conclusion from the NMR adsorption experiment that electron transfer in these systems occurs within statically adsorbed QD-molecule complexes.

The time constant for electron transfer from the QD to [PHA H]$^+$ is much longer than that for the other two substrates. In fact, in the case of the QD-PHA sample, it was not possible to deconvolute the electron transfer time constant from one of the electron trapping time constants, so it was concluded that this time constant is on the 100 ns time scale. This time constant could, in principle, reflect a diffusion-limited process, but on the basis of the NMR result that, under acidic conditions, [PHA H]$^+$ has a very similar affinity for the QD surface to those of [NB H]$^+$ and [NSB H]$^+$, it can reasonably be concluded that the relatively slow electron transfer to [PHA H]$^+$ is due to (i) the smaller driving force for its reduction or (ii) the contribution of proton transfer to the observed rate, since, at pH 3.6, only 17% of PHA molecules are protonated (as opposed to 60% of NB and 40% of NSB).

In order to physically interpret the trend in rate constants for electron transfer to the catalytic substrates, we must convert the observed rate constant to the "intrinsic" rate constant, $k_{eT,int}$, for each reaction. Observed rate constants for charge separation between QDs and molecules scale linearly with the number of electron-accepting molecules bound per QD. The intrinsic rate constant is the single donor-single acceptor rate constant, which is the number that is correlated with the driving force and electronic coupling for the electron transfer reaction through the Marcus equation (ref. 74; incorporated by reference in its entirety). The intrinsic rate constant is simply the observed rate constant divided by the number of adsorbed acceptors per QD, which we estimate from the NMR data in Table 4. The values of $k_{eT,int}$ are $7.3 \times 10^6$ s$^{-1}$ for the QD–[NB H]$^+$ donor-acceptor pair, $1.6 \times 10^7$ s$^{-1}$ for the QD–[NSB H]$^+$ pair, and $<3.4 \times 10^4$ s$^{-1}$ for the QD–[PHA H]$^+$ pair (Table 3).

TABLE 5

Summary of the Measured Intrinsic Rate Constants for
One-Electron Transfers from QD$^-$

| electron acceptor (X) | reduction potential of X (V vs NHE) | $k_{eT,int}$ (s$^{-1}$) for the reaction QD$^-$ + X → QD + X$^-$ |
|---|---|---|
| [NB H]$^+$ | −0.16 | 7.3 × 10$^6$ |
| [NSB H]$^+$ | +0.29 | 1.6 × 10$^7$ |
| [PHA H]$^+$ | −0.46 | <3.4 × 10$^4$ |

The rate constants for electron transfer, $k_{eT,int}$(QD−[NSB H]$^+$)>$k_{eT,int}$(QD−[NB H]$^+$)>$k_{eT,int}$(QD−[PHA H]$^+$), are correlated with the magnitudes of the driving forces for the corresponding proton-coupled two-electron reactions:|ΔG$_{eT}$ (QD−[NSB H]$^+$)|>|ΔG$_{eT}$(QD−[NB H]$^+$)|>|ΔG$_{eT}$(QD−[PHA H]$^+$)| (ref. B60; incorporated by reference in its entirety). These driving forces are best approximated as the reduction potential of the QD, which has been reported in the range from −0.8 to −2.0 V vs NHE (refs. 64, 76, 77; incorporated by reference in their entireties) minus the reduction potential of the substrate (+0.29 V vs NHE for NSB, −0.16 V vs NHE for NB, and −0.46 V vs NHE for PHA) (ref. 60; incorporated by reference in its entirety), since the electron transfer occurs from the QD anion (formed upon scavenging of the hole by MPA) to the substrate. This correspondence between the rate constant and thermodynamic driving force is not necessarily expected, since the TA measures the rate of the one-electron reaction and the potentials are for the two-electron reaction and since recruitment of protons for these reactions could contribute to an overpotential that would influence the observed rate. This correlation would indicate that (i) the driving forces for each electron transfer within a two-electron step are very similar (a result corroborated by cyclic voltammetry) and (ii) electron transfer, rather than proton transfer, is rate-limiting (ref. 42; incorporated by reference in its entirety).

From the amplitudes of the electron transfer components in the TA spectra, the internal quantum yield of electron transfer was estimated from the QD to NB (0.31) and to NSB (0.44). The average amplitude of 0.38 agrees well with the average internal quantum yield we independently measure with GC-MS (0.37) and in constructing the action spectrum in FIG. 3 (0.34 at 400 nm).

REFERENCES

The following references, some of which are also referenced above, are herein incorporated by reference in its entirety.

A1. Worrell, E., Phylipsen, D., Einstein, D. & Martin, N. Energy use and energy intensity of the U.S. chemical industry. 1-40 (2000).
A2. Han, Z., Qiu, F., Eisenberg, R., Holland, P. L. & Krauss, T. D. Robust Photogeneration of H2 in Water Using Semiconductor Nanocrystals and a Nickel Catalyst. Science 338, 1321-1324 (2012).
A3. Yang, H. B. et al. Stable Quantum Dot Photoelectrolysis Cell for Unassisted Visible Light Solar Water Splitting. ACS Nano 8, 10403-10413 (2014).
A4. Brown, K. A., Wilker, M. B., Boehm, M., Dukovic, G. & King, P. W. Characterization of Photochemical Processes for H 2 Production by CdS Nanorod—(FeFe) Hydrogenase Complexes. J. Am. Chem. Soc. 134, 5627-5636 (2012).
A5. Maldotti, A. et al. Photochemical and photocatalytic reduction of nitrobenzene in the presence of cyclohexene. 'Journal of Photochemistry & Photobiology, A: Chemistry' 133, 129-133 (2000).
A6. Eskandari, P., Kazemi, F. & Zand, Z. Photocatalytic reduction of aromatic nitro compounds using CdS nanostructure under blue LED irradiation. 'Journal of Photochemistry & Photobiology, A: Chemistry' 274, 7-12 (2014).
A7. Sarasa, J. et al. Treatment of a wastewater resulting from dyes manufacturing with ozone and chemical coagulation. Water Research 32, 2721-2727 (1998).
A8. Soares, B. G., Amorim, G. S., Souza, F. G., Jr., Oliveira, M. G. & Silva, J. E. P. D. The in situ polymerization of aniline in nitrile rubber. Synthetic Metals 156, 91-98 (2006).
A9. Pezzatini, G. & Guidelli, R. Double-layer structure and mechanism of electrode reactions: Part II. Nitrobenzene reduction on mercury from aqueous solutions. J. Electroanal. Chem. (1979).
A10. Scherer, M. M., Johnson, K. M., Westall, J. C. & Tratnyek, P. G. Mass Transport Effects on the Kinetics of Nitrobenzene Reduction by Iron Metal. Environ. Sci. Technol. 35, 2804-2811 (2001).
A11. Li, Y.-P., Cao, H.-B., Liu, C.-M. & Zhang, Y. Electrochemical reduction of nitrobenzene at carbon nanotube electrode. Journal of Hazardous Materials 148, 158-163 (2007).
A12. Haram, S. K., Quinn, B. M. & Bard, A. J. Electrochemistry of CdS Nanoparticles: A Correlation between Optical and Electrochemical Band Gaps. J. Am. Chem. Soc. 123, 8860-8861 (2001).
A13. Colvin, V. L., Alivisatos, A. P. & Tobin, J. G. Valence-Band Photoemission From a Quantum-Dot System. Phys. Rev. Lett. 66, 2786-2789 (1991).
A14. WUBBELS, G. G., JORDAN, J. W. & MILLS, N. S. Hydrochloric-Acid Catalyzed Photoreduction of Nitrobenzene by 2-Propanol—Question of Protonation in Excited-State. Abstracts of Papers of the American Chemical Society 164, 18-& (1972).
A15. Kröhl, O., Malsch, K. & Swiderek, P. The electronic states of nitrobenzene: electron-energy-loss spectroscopy and CASPT2 calculations. Phys. Chem. Chem. Phys. 2, 947-953 (2000).
A16. Hens, Z. & Martins, J. C. A Solution NMR Toolbox for Characterizing the Surface Chemistry of Colloidal Nanocrystals. Chem. Mater. 25, 1211-1221 (2013).
A17. Moreels, I. et al. Size-Tunable, Bright, and Stable PbS Quantum Dots: A Surface Chemistry Study. ACS Nano 5, 2004-2012 (2011).
A18. Sachleben, J. R., Colvin, V., Emsley, L., Wooten, E. W. & Alivisatos, A. P. Solution-State NMR Studies of the Surface Structure and Dynamics of Semiconductor Nanocrystals. J. Phys. Chem. B 102, 10117-10128 (1998).
A19. Terrill, R. H. et al. Monolayers in three dimensions: NMR, SAXS, thermal, and electron hopping studies of alkanethiol stabilized gold clusters. J. Am. Chem. Soc. 117, 12537-12548 (1995).
B1. Gould, T. J.; Hess, S. T.; Bewersdorf, J. Z. Phys. Chem. 2008, 222, 833.
B2. Yehezkeli, O.; de Oliveira, D. R. B.; Cha, J. N. Small 2015, 11, 668.
B3. Das, A.; Han, Z. J.; Haghighi, M. G.; Eisenberg, R. Proc. Natl. Acad. Sci. U.S.A 2013, 110, 16716.
B4. Yu, W. W.; Qu, L.; Guo, W.; Peng, X. Chem. Mater. 2003, 15, 2854.

B5. Dukovic, G.; Merkle, M. G.; Nelson, J. H.; Hughes, S. M.; Alivisatos, A. P. Adv. Mater. 2008, 20, 4306.

B6. Eggins, B. R.; Irvine, J. T. S.; Murphy, E. P.; Grimshaw, J. J. Chem. Soc., Chem. Commun. 1988, 1123.

B7. Kumar, A.; Kumar, S. J. Phys. Org. Chem. 1998, 11, 277.

B8. Shiragami, T.; Ankyu, H.; Fukami, S.; Pac, C.; Yanaglda, S.; Mori, H.; Fujita, H. J. Chem. Soc., Faraday Trans. 1992, 88, 1055.

B9. Inoue, H.; Yamachika, M.; Yoneyama, H. J. Chem. Soc., Faraday Trans. 1992, 88, 2215.

B10. Yanagida, S.; Shindo, A.; Hosokawa, H.; Mori, H.; Sakata, T.; Wada, Y.; Ogata, T. Bull. Chem. Soc. Jpn. 1995, 68, 752.

B11. Pal, B.; Torimoto, T.; Iwasaki, K.; Shibayama, T.; Takahashi, H.; Ohtani, B. J. Phys. Chem. B 2004, 108, 18670.

B12. Hosokawa, H.; Wada, Y.; Murakoshi, K.; Sakata, T.; Mori, H.; Yanagida, S.; Ogata, T. J. Chem. Soc., Faraday Trans. 1996, 92, 4575.

B13. Hoffman, A. J.; Mills, G.; Yee, H.; Hoffmann, M. R. J. Phys. Chem. 1992, 96, 5546.

B14. Kuehnel, M. F.; Wakerley, D. W.; Orchard, K. L.; Reisner, E. Angew. Chem., Int. Ed. 2015, 54, 9627.

B15. Nedeljkovic, J. M.; Nenadovic, M. T.; Micic, O. I.; Nozik, A. J. J. Phys. Chem. 1986, 90, 12.

B16. Kisch, H. Angew. Chem., Int. Ed. 2013, 52, 812.

B17. Chen, X. B.; Shen, S. H.; Guo, L. J.; Mao, S. S. Chem. Rev. 2010, 110, 6503.

B18. Osterloh, F. E. Chem. Mater. 2008, 20, 35.

B19. Wilker, M. B.; Schnitzenbaumer, K. J.; Dukovic, G. Isr. J. Chem. 2012, 52, 1002.

B20. Harris, L. A.; Wilson, R. H. Annu. Rev. Mater. Sci. 1978, 8, 99.

B21. Chaudhary, Y. S.; Woolerton, T. W.; Allen, C. S.; Warner, J. H.; Pierce, E.; Ragsdale, S. W.; Armstrong, F. A. Chem. Commun. 2012, 48, 58.

B22. Huang, J.; Mulfort, K. L.; Du, P. W.; Chen, L. X. J. Am. Chem. Soc. 2012, 134, 16472.

B23. Zhu, H. M.; Song, N. H.; Lv, H. J.; Hill, C. L.; Lian, T. Q. J. Am. Chem. Soc. 2012, 134, 11701.

B24. Yu, W. L.; Noureldine, D.; Isimjan, T.; Lin, B.; Del Gobbo, S.; Abulikemu, M.; Hedhili, M. N.; Anjum, D. H.; Takanabe, K. Phys. Chem. Chem. Phys. 2015, 17, 1001.

B25. Gimbert-Surinach, C.; Stoll, T.; Fortage, J.; Collomb, M. N.; Deronzier, A.; Palomares, E.; Llobet, A.; Albero, J. J. Am. Chem. Soc. 2014, 136, 7655.

B26. Li, Z. J.; Wang, J. J.; Li, X. B.; Fan, X. B.; Meng, Q. Y.; Feng, K.; Chen, B.; Tung, C. H.; Wu, L. Z. Adv. Mater. 2013, 25, 6613.

B27. Han, Z. J.; Qiu, F.; Eisenberg, R.; Holland, P. L.; Krauss, T. D. Science 2012, 338, 1321.

B28. Liu, C.; Qiu, F.; Peterson, J. J.; Krauss, T. D. J. Phys. Chem. B 2015, 119, 7349.

B29. Meng, P.; Wang, M.; Yang, Y.; Zhang, S.; Sun, L. J. Mater. Chem. A 2015, 3, 18852.

B30. Shemesh, Y.; Macdonald, J. E.; Menagen, G.; Banin, U. Angew. Chem., Int. Ed. 2011, 50, 1185.

B31. Brown, K. A.; Dayal, S.; Ai, X.; Rumbles, G.; King, P. W. J. Am. Chem. Soc. 2010, 132, 9672.

B32. Brown, K. A.; Wilker, M. B.; Boehm, M.; Dukovic, G.; King, P. W. J. Am. Chem. Soc. 2012, 134, 5627.

B33. Wang, F.; Wang, W.-G.; Wang, X.-J.; Wang, H.-Y.; Tung, C.-H.; Wu, L.-Z. Angew. Chem., Int. Ed. 2011, 50, 3193.

B34. Liang, W.-J.; Wang, F.; Wen, M.; Jian, J.-X.; Wang, X.-Z.; Chen, B.; Tung, C.-H.; Wu, L.-Z. Chem.-Eur. J. 2015, 21, 3187.

B35. Greene, B. L.; Joseph, C. A.; Maroney, M. J.; Dyer, R. B. J. Am. Chem. Soc. 2012, 134, 11108.

B36. de Mello Donega, C.; Bode, M.; Meijerink, A. Phys. Rev. B: Condens. Matter Mater. Phys. 2006, 74, 085320.

B37. Knowles, K. E.; Malicki, M.; Parameswaran, R.; Cass, L. C.; Weiss, E. A. J. Am. Chem. Soc. 2013, 135, 7264.

B38. Cass, L. C.; Swenson, N. K.; Weiss, E. A. J. Phys. Chem. C 2014, 118, 18263.

B39. Peterson, M. D.; Jensen, S. C.; Weinberg, D. J.; Weiss, E. A. ACS Nano 2014, 8, 2826.

B40. Resch-Genger, U.; Grabolle, M.; Cavaliere-Jaricot, S.; Nitschke, R.; Nann, T. Nat. Methods 2008, 5, 763.

B41. ten Cate, S.; Sandeep, C. S. S.; Liu, Y.; Law, M.; Kinge, S.; Houtepen, A. J.; Schins, J. M.; Siebbeles, L. D. A. Acc. Chem. Res. 2015, 48, 174.

B42. Zhao, J.; Osterloh, F. E.; Holmes, M. A. ACS Nano 2013, 7, 4316-4325.

B43. Bernt, C. M.; DeMartino, A. W.; Pierri, A. E.; Levy, E. S.; Zigler, D. F.; Ford, P. C.; Burks, P. T. J. Am. Chem. Soc. 2014, 136, 2192.

B44. Li, X.-B.; Li, Z.-J.; Gao, Y.-J.; Meng, Q.-Y.; Yu, S.; Weiss, R. G.; Tung, C.-H.; Wu, L.-Z. Angew. Chem., Int. Ed. 2014, 53, 2085.

B45. Pal, B.; Torimoto, T.; Okazaki, K.; Ohtani, B. Chem. Commun. 2007, 483.

B46. Warrier, M.; Lo, M. K. F.; Monbouquette, H.; Garcia-Garibay, M. A. Photochem. Photobiol. Sci. 2004, 3, 859.

B47. Eskandari, P.; Zand, Z.; Kazemi, F. J. Photochem. Photobiol., A 2014, 274, 7.

B48. Schrauben, J. N.; Hayoun, R.; Valdez, C. N.; Braten, M.; Fridley, L.; Mayer, J. M. Science 2012, 336, 1298.

B49. Hoffman, A. J.; Yee, H.; Mills, G.; Hoffmann, M. R. J. Phys. Chem. 1992, 96, 5540.

B50. Chauvire, T.; Gasparutto, D.; Ravanat, J.-L.; Lebrun, C.; Gromova, M.; Jouneau, P.-H.; Chauvin, J.; Gambarelli, S.; Maurel, V.; Mouesca, J.-M. J. Phys. Chem. C 2015, 119, 17857.

B51. Morris-Cohen, A. J.; Malicki, M.; Peterson, M. D.; Slavin, J. J. W.; Weiss, E. A. Chem. Mater. 2013, 25, 1155.

B52. Smith, W. H.; Bard, A. J. J. Am. Chem. Soc. 1975, 97, 5203.

B53. Frederick, M. T.; Weiss, E. A. ACS Nano 2010, 4, 3195.

B54. Ben, M. J.; Vaneski, A.; Mauser, C.; Fischbach, S.; Susha, A. S.; Rogach, A. L.; Jackel, F.; Feldmann, J. Small 2012, 8, 291.

B55. Amirav, L.; Alivisatos, A. P. J. Am. Chem. Soc. 2013, 135, 13049.

B56. Acharya, K. P.; Khnayzer, R. S.; O'Connor, T.; Diederich, G.; Kirsanova, M.; Klinkova, A.; Roth, D.; Kinder, E.; Imbo-den, M.; Zamkov, M. Nano Lett. 2011, 11, 2919.

B57. Iwasita, T. Electrochim. Acta 2002, 47, 3663.

B58. Forlano, P.; Olabe, J. A.; Magallanes, J. F.; Blesa, M. A. Can. J. Chem. 1997, 75, 9.

B59. Maldotti, A.; Andreotti, L.; Molinari, A.; Tollari, S.; Penoni, A.; Cenini, S. J. Photochem. Photobiol., A 2000, 133, 129.

B60. Li, Y.-P.; Cao, H.-B.; Liu, C.-M.; Zhang, Y. J. Hazard. Mater. 2007, 148, 158.

B61. Scifinder-calculated using ACD/Labs Software, Chemical Abstracts Service, 2015.

B62. Croston, M.; Langston, J.; Takacs, G.; Morrill, T. C.; Miri, M.; Santhanam, K. S. V.; Ajayan, P. Int. J. Nanosci. 2002, 1, 285.

B63. Hurley, R.; Testa, A. C. J. Am. Chem. Soc. 1966, 88, 4330.
B64. Haram, S. K.; Quinn, B. M.; Bard, A. J. J. Am. Chem. Soc. 2001, 123, 8860.
B65. Lund, H. Organic Electrochemistry; 4th ed.; Marcel Dekker: New York, 2001.
B66. Cass, L. C.; Malicki, M.; Weiss, E. A. Anal. Chem. 2013, 85, 6974.
B67. Malicki, M.; Knowles, K. E.; Weiss, E. A. Chem. Commun. 2013, 49, 4400.
B68. Knowles, K. E.; Peterson, M. D.; McPhail, M. R.; Weiss, E. A. J. Phys. Chem. C 2013, 117, 10229.
B69. Knowles, K. E.; McArthur, E. A.; Weiss, E. A. ACS Nano 2011, 5, 2026.
B70. McArthur, E. A.; Morris-Cohen, A. J.; Knowles, K. E.; Weiss, E. A. J. Phys. Chem. B 2010, 114, 14514.
B71. Cooney, R. R.; Sewall, S. L.; Dias, E. A.; Sagar, D. M.; Anderson, K. E. H.; Kambhampati, P. Phys. Rev. B: Condens. Matter Mater. Phys. 2007, 75, 245311.
B72. Klimov, V. I.; Schwarz, C. J.; McBranch, D. W.; Leatherdale, C. A.; Bawendi, M. G. Phys. Rev. B: Condens. Matter Mater. Phys. 1999, 60, R2177.
B73. Boulesbaa, A.; Stockwell, D.; Huang, Z.; Huang, J.; Guo, J.; Lian, T.; Issac, A. J. Am. Chem. Soc. 2007, 129, 15132.
B74. Morris-Cohen, A. J.; Frederick, M. T.; Cass, L. C.; Weiss, E. A. J. Am. Chem. Soc. 2011, 133, 10146.
B75. Zhu, H.; Yang, Y.; Hyeon-Deuk, K.; Califano, M.; Song, N.; Wang, Y.; Zhang, W.; Prezhdo, O. V.; Lian, T. Nano Lett. 2014, 14, 1263.
B76. Chi, Y.; Fu, H.; Qi, L.; Shi, K.; Zhang, H.; Yu, H. J. Photochem. Photobiol., A 2008, 195, 357.
B77. Korgel, B. A.; Monbouquette, H. G. J. Phys. Chem. B 1997, 101, 5010.
B78. Chang, C. M.; Orchard, K. L.; Martindale, B. C. M.; Reisner, E. J. Mater. Chem. A 2016, DOI: 10.1039/C5TA04136H.
B79. Lee, J. M.; Ham, Y.; Kim, I. Y.; Domen, K.; Hwang, S.-J.; Gunjakar, J. L. Chem.-Eur. J. 2014, 20, 17004.
B80. Perera, D.; Lorek, R.; Khnayzer, R. S.; Moroz, P.; O'Connor, T.; Khon, D.; Diederich, G.; Kinder, E.; Lambright, S.; Castellano, F. N.; Zamkov, M. J. Phys. Chem. C 2012, 116, 22786.
B81. Huang, J.; Huang, Z.; Jin, S.; Lian, T. Q. J. Phys. Chem. C 2008, 112, 19734.

The invention claimed is:

1. A system comprising:
    (a) a 3-mercaptopropionic acid (3-MPA)-capped cadmium sulfide (CdS) quantum dot (QD); and
    (b) a nitrobenzene compound.
2. The system of claim 1, wherein the nitrobenzene compound is selected from the group consisting of: nitrobenzene, 4-nitrobenzoic acid, methyl 4-nitrobenzoate, 1-chloro-4-nitrobenzene, 1-fluoro-4-nitrobenzene, 4-nitroaniline, 1-tertbutyl-4-nitrobenzene, 2,4,6-tri-tertbutyl-nitrobenzene, 1,3-dimethyl-2-nitrobenzene, 1,3-dimethyl-5-nitrobenzene, 2,4,6-trinitrotoluene, 2,4-dinitrotoluene, 2,6-dinitrotoluene, 2,3-dinitrotoluene, 2,5-dinitrotoluene, 3,4-dinitrotoluene, 3,5-dinitrotoluene, 1,3,5-trinitrobenzene, 2,4,6-trinitrophenol, and 2,4,6-trinitro-1,3-benzenediol.
3. The system of claim 1, further comprising one or more solvents.
4. The system of claim 3, wherein the one or more solvents comprise water and/or methanol.
5. The system of claim 1, further comprising an aniline.
6. The system of claim 5, wherein the aniline is selected from the group consisting of: aniline, 4-aminobenzoic acid, methyl 4-aminobenzoate, 1-chloro-4-aminobenzene, 1-fluoro-4-aminobenzene, 4-aminoaniline, 1-tertbutyl-4-aminobenzene, 2,4,6-tri-tertbutyl-aminobenzene, 1,3-dimethyl-2-aminobenzene, 1,3-dimethyl-5-aminobenzene, 2,4,6-triaminotoluene, 2,4-diaminotoluene, 2,6-diaminotoluene, 2,3-diaminotoluene, 2,5-diaminotoluene, 3,4-diaminotoluene, 3,5-diaminotoluene, 1,3,5-triaminobenzene, 2,4,6-triaminophenol, and 2,4,6-triamino-1,3-benzenediol.
7. The system of claim 1, having a pH below 6.0.
8. The system of claim 1, having a pH between 2 and 5.
9. The system of claim 1, wherein the cadmium sulfide quantum dot is in solution.
10. The system of claim 1, further comprising a surface, wherein the cadmium sulfide quantum dot is adhered to the surface.
11. The system of claim 10, wherein the surface is the interior of a vessel.
12. A method of reducing a nitrobenzene to an aniline comprising illuminating a system of claim 1 with light at a wavelength between 350 nm and 450 nm.
13. The method of claim 12, wherein the light is at a wavelength between 395 nm and 415 nm.
14. The method of claim 12, wherein the aniline is produced from the nitrobenzene through a phenylhydroxylamine intermediate.

* * * * *